(12) United States Patent
Abdou

(10) Patent No.: US 7,828,847 B2
(45) Date of Patent: Nov. 9, 2010

(54) DEVICES AND METHODS FOR INTER-VERTEBRAL ORTHOPEDIC DEVICE PLACEMENT

(76) Inventor: Samy Abdou, 7790 Doug Hill, San Diego, CA (US) 92127

( * ) Notice: Subject to any disclaimer, the term of this patent is extended or adjusted under 35 U.S.C. 154(b) by 0 days.

(21) Appl. No.: 11/675,597

(22) Filed: Feb. 15, 2007

(65) Prior Publication Data

US 2007/0191958 A1  Aug. 16, 2007

Related U.S. Application Data

(60) Provisional application No. 60/773,584, filed on Feb. 15, 2006, provisional application No. 60/850,473, filed on Oct. 10, 2006, provisional application No. 60/874,195, filed on Dec. 11, 2006.

(51) Int. Cl.
*A61F 2/44* (2006.01)
(52) U.S. Cl. ............... 623/17.13; 623/17.11; 623/17.14; 623/17.15
(58) Field of Classification Search ................... 606/61; 623/17.11–17.16
See application file for complete search history.

(56) References Cited

U.S. PATENT DOCUMENTS

| | | | |
|---|---|---|---|
| 4,759,769 A | 7/1988 | Hedman et al. | |
| 4,997,432 A | 3/1991 | Keller | |
| 5,425,773 A * | 6/1995 | Boyd et al. | 623/17.15 |
| 5,514,180 A | 5/1996 | Heggeness et al. | |
| 5,556,431 A | 9/1996 | Buttner-Janz | |
| 5,562,738 A | 10/1996 | Boyd et al. | |
| 5,674,294 A | 10/1997 | Bainville et al. | |
| 5,674,296 A | 10/1997 | Bryan et al. | |
| 5,676,701 A | 10/1997 | Yuan et al. | |
| 5,976,186 A | 11/1999 | Bao et al. | |
| 6,001,130 A | 12/1999 | Bryan et al. | |
| 6,019,792 A | 2/2000 | Cauthen | |
| 6,022,376 A | 2/2000 | Assell et al. | |
| 6,093,205 A | 7/2000 | McLeod et al. | |
| 6,355,038 B1 | 3/2002 | Pisharodi | |
| 6,419,706 B1 | 7/2002 | Graf | |
| 6,440,168 B1 | 8/2002 | Cauthen | |
| 6,461,359 B1 | 10/2002 | Tribus et al. | |
| 6,610,093 B1 | 8/2003 | Pisharodi | |
| 6,679,915 B1 | 1/2004 | Cauthen | |
| 6,706,068 B2 | 3/2004 | Ferree | |
| 6,709,461 B2 | 3/2004 | O'Neil et al. | |
| 6,723,127 B2 | 4/2004 | Ralph et al. | |
| 6,749,635 B1 | 6/2004 | Bryan | |
| 6,758,861 B2 | 7/2004 | Ralph et al. | |
| 6,764,515 B2 | 7/2004 | Ralph et al. | |

(Continued)

FOREIGN PATENT DOCUMENTS

WO  WO 07/095333  8/2007

(Continued)

*Primary Examiner*—Eduardo C Robert
*Assistant Examiner*—Julianna N Harvey
(74) *Attorney, Agent, or Firm*—Fred C. Hernandez; Mintz, Levin, Cohn, Ferris, Glovsky and Popeo, P.C.

(57) ABSTRACT

A bone prosthesis device is comprised of an upper and lower abutment surfaces and an intervening malleable member. The device is sufficiently small so that implantation into an inter-vertebral disc space can be performed from a substantially posterior approach without significant impingement upon the neural elements.

11 Claims, 35 Drawing Sheets

U.S. PATENT DOCUMENTS

| | | |
|---|---|---|
| 7,083,622 B2 | 8/2006 | Simonson |
| 7,083,649 B2 | 8/2006 | Zucherman et al. |
| 7,101,399 B2 | 9/2006 | Errico et al. |
| 7,128,761 B2 | 10/2006 | Kuras et al. |
| 7,204,853 B2 | 4/2007 | Gordon et al. |
| 7,273,496 B2 | 9/2007 | Mitchell |
| 7,316,714 B2 | 1/2008 | Gordon et al. |
| 7,331,995 B2 | 2/2008 | Eisermann et al. |
| 2001/0039452 A1* | 11/2001 | Zucherman et al. ...... 623/17.11 |
| 2003/0065395 A1* | 4/2003 | Ralph et al. ............. 623/17.13 |
| 2003/0078662 A1* | 4/2003 | Ralph et al. ............. 623/17.13 |
| 2003/0176923 A1 | 9/2003 | Keller et al. |
| 2003/0208273 A1 | 11/2003 | Eisermann et al. |
| 2004/0220670 A1 | 11/2004 | Eisermann et al. |
| 2004/0225364 A1* | 11/2004 | Richelsoph et al. ...... 623/17.13 |
| 2004/0225365 A1 | 11/2004 | Eisermann et al. |
| 2004/0225366 A1 | 11/2004 | Eisermann et al. |
| 2004/0236425 A1* | 11/2004 | Huang ..................... 623/17.12 |
| 2004/0243240 A1 | 12/2004 | Beaurain et al. |
| 2004/0267369 A1 | 12/2004 | Lyons et al. |
| 2005/0033431 A1* | 2/2005 | Gordon et al. ........... 623/17.11 |
| 2005/0043800 A1 | 2/2005 | Paul et al. |
| 2005/0043802 A1 | 2/2005 | Eisermann et al. |
| 2005/0071007 A1* | 3/2005 | Malek ..................... 623/17.11 |
| 2005/0125066 A1 | 6/2005 | McAfee |
| 2005/0165487 A1 | 6/2005 | Muhanna et al. |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0192671 A1 | 9/2005 | Bao et al. |
| 2005/0197702 A1 | 9/2005 | Coppes et al. |
| 2005/0222682 A1 | 10/2005 | Link et al. |
| 2005/0234555 A1 | 10/2005 | Sutton et al. |
| 2005/0240273 A1 | 10/2005 | Khandkar et al. |
| 2005/0256576 A1 | 11/2005 | Moskowitz et al. |
| 2005/0283241 A1 | 12/2005 | Keller et al. |
| 2006/0084988 A1 | 4/2006 | Kim |
| 2006/0106395 A1 | 5/2006 | Link et al. |
| 2006/0116768 A1 | 6/2006 | Krueger et al. |
| 2006/0178746 A1 | 8/2006 | Bartish, Jr. et al. |
| 2006/0190082 A1 | 8/2006 | Keller et al. |
| 2006/0195192 A1 | 8/2006 | Gordon et al. |
| 2006/0217809 A1* | 9/2006 | Albert et al. ............. 623/17.11 |
| 2006/0276900 A1 | 12/2006 | Carpenter |
| 2007/0021836 A1 | 1/2007 | Doty |
| 2007/0162133 A1 | 6/2007 | Doubler et al. |
| 2007/0161992 A1* | 7/2007 | Kwak et al. ................... 606/61 |
| 2007/0191958 A1 | 8/2007 | Abdou |
| 2007/0282448 A1 | 12/2007 | Abdou |
| 2008/0015698 A1 | 1/2008 | Marino |
| 2008/0039843 A1 | 2/2008 | Abdou |

FOREIGN PATENT DOCUMENTS

| | | |
|---|---|---|
| WO | WO 07/140382 | 12/2007 |
| WO | WO 08/021319 | 2/2008 |
| WO | WO 08/073447 | 6/2008 |

\* cited by examiner

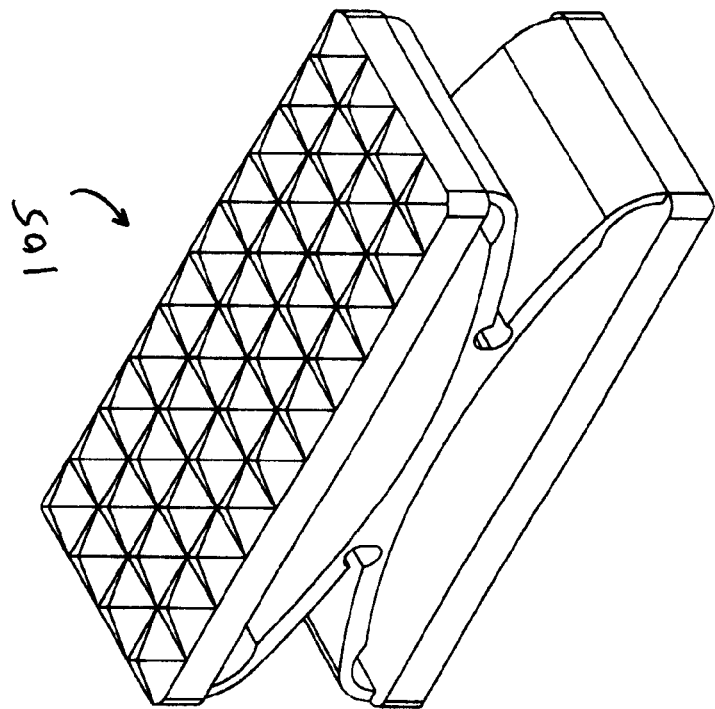
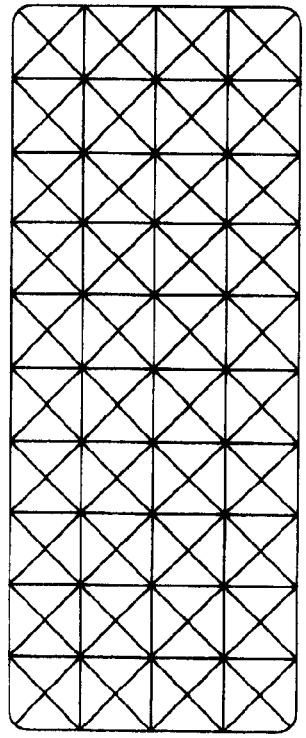
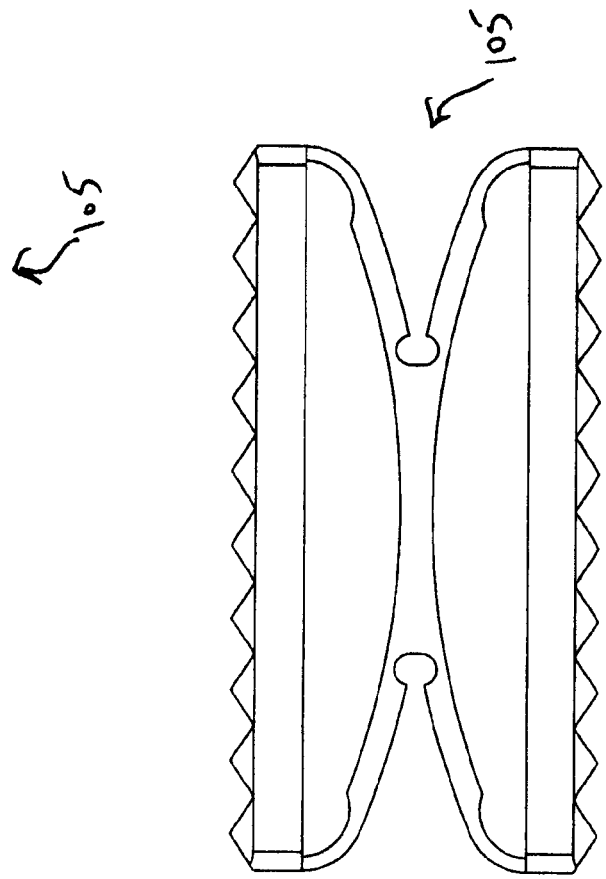
Fig. 2

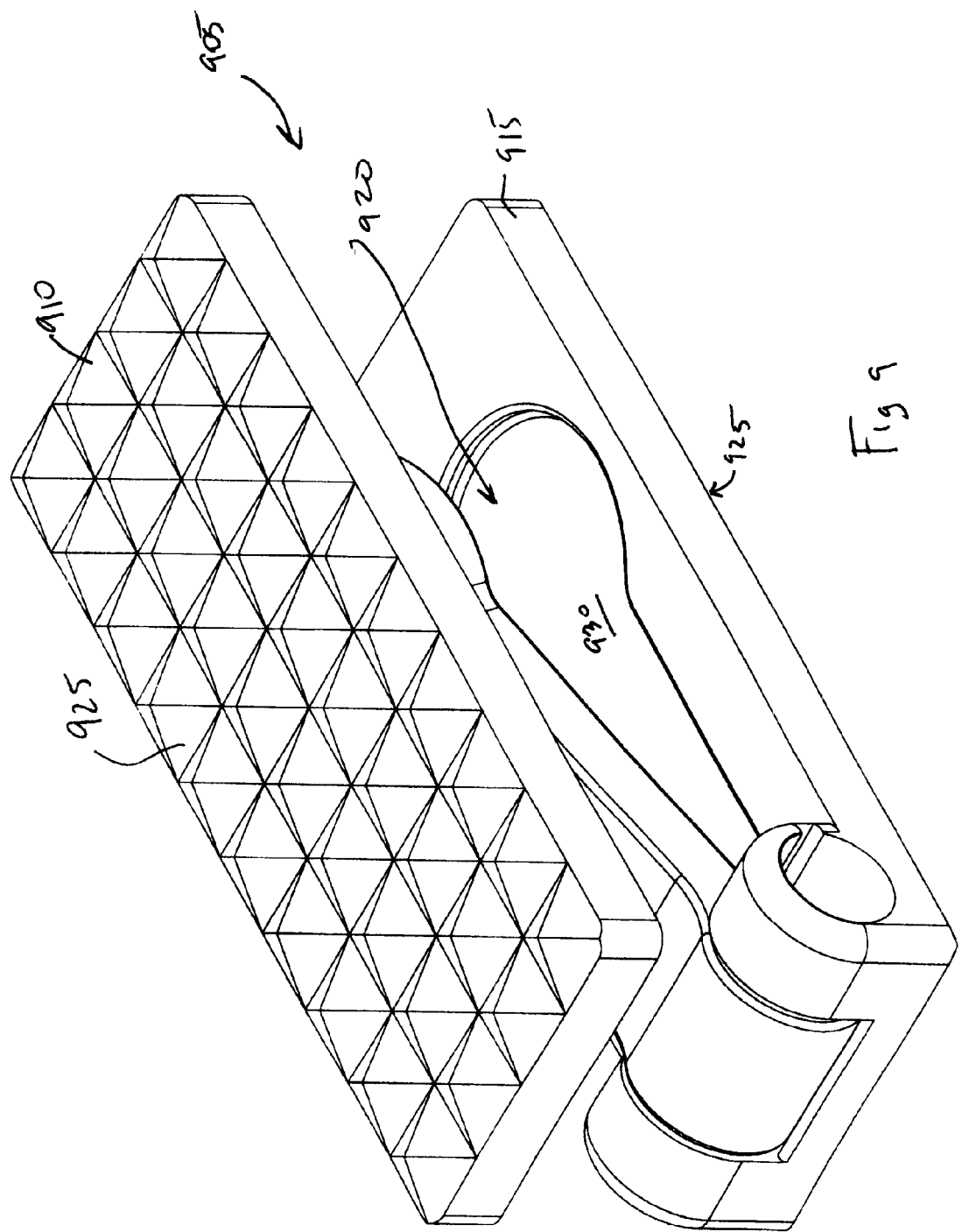

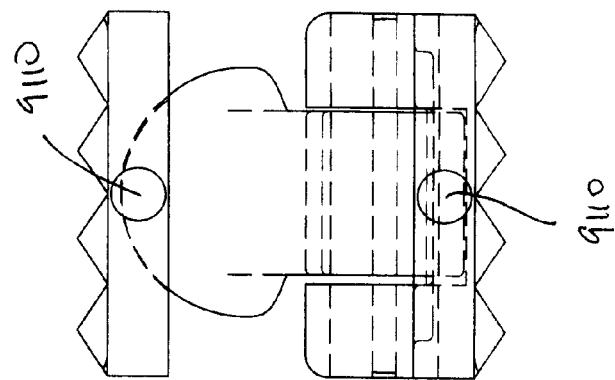
Figure 10
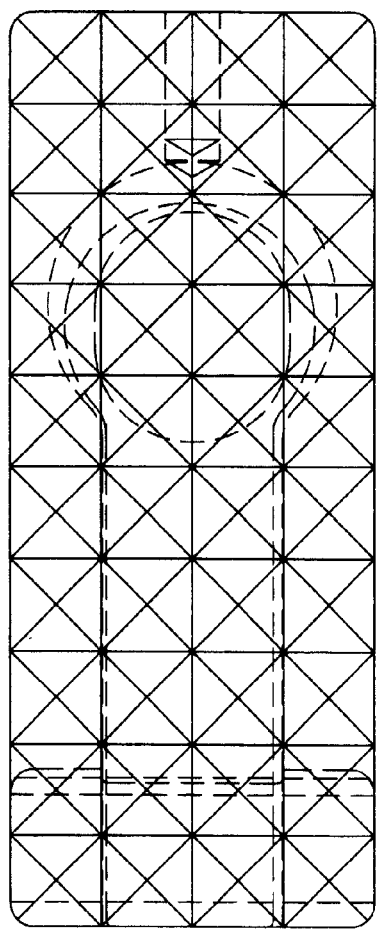
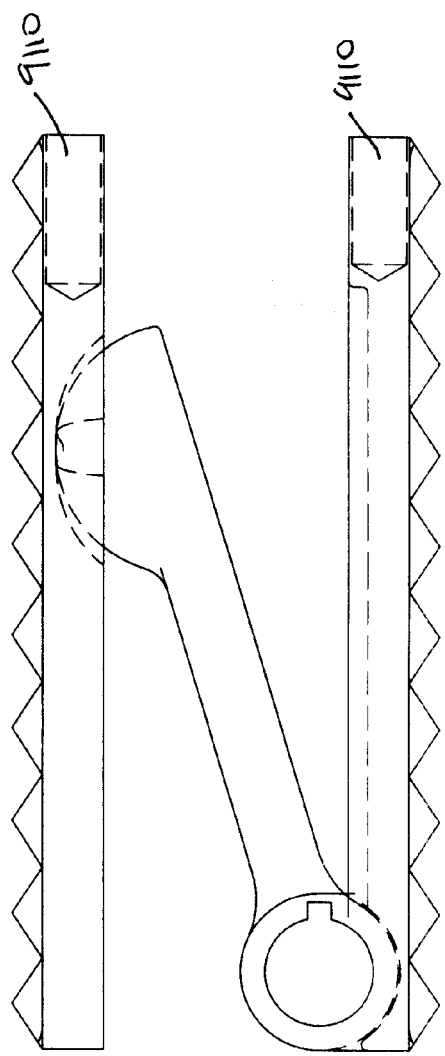

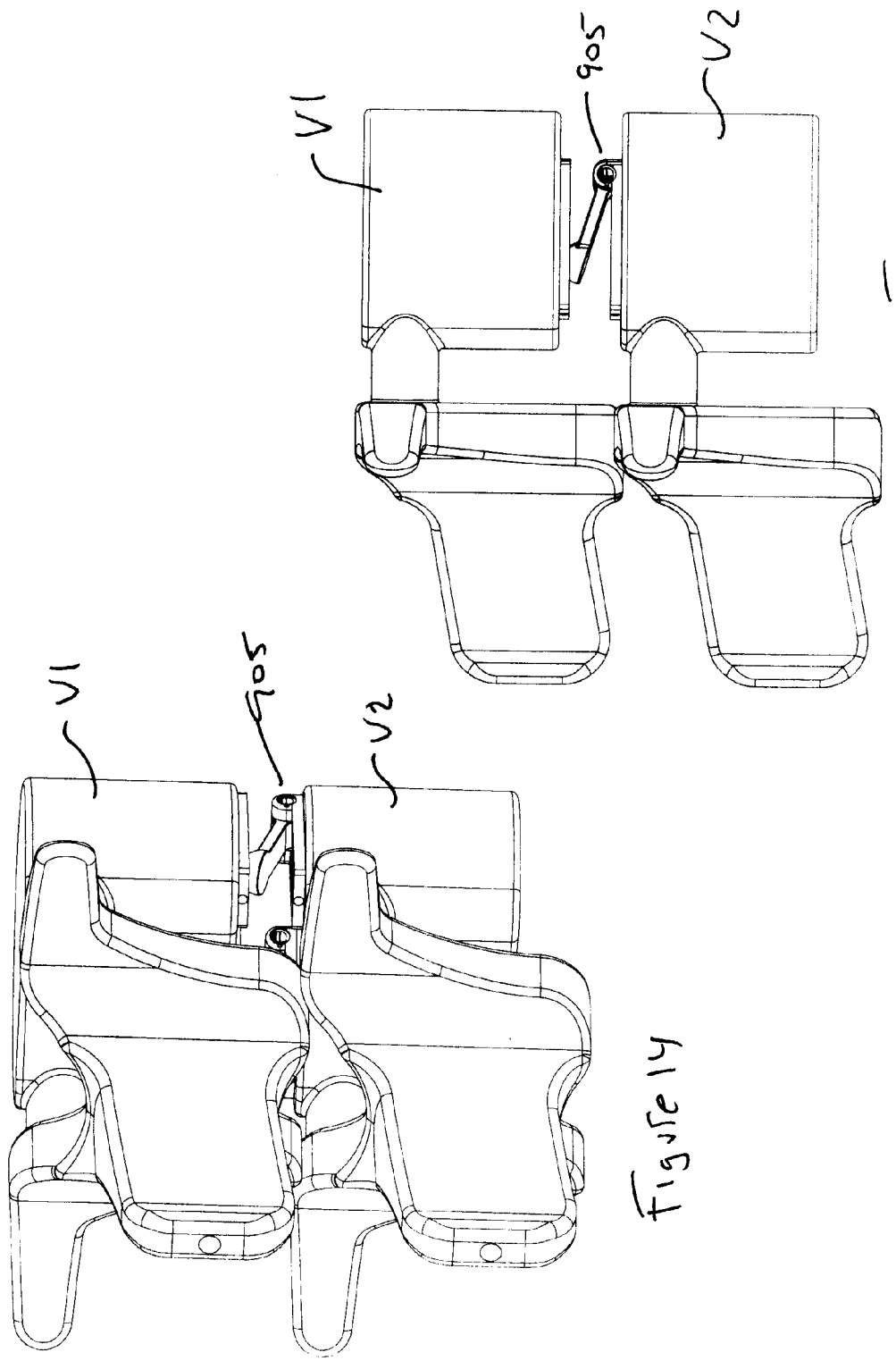

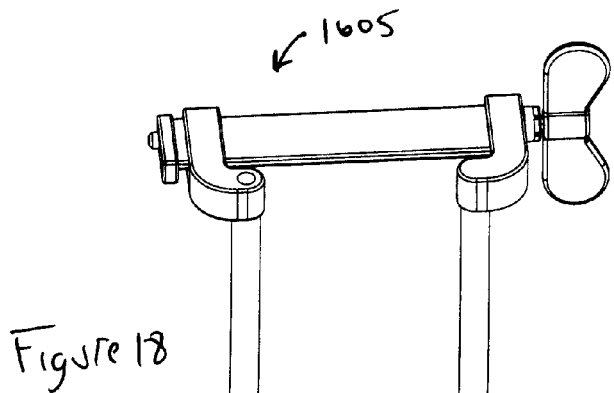
Figure 18
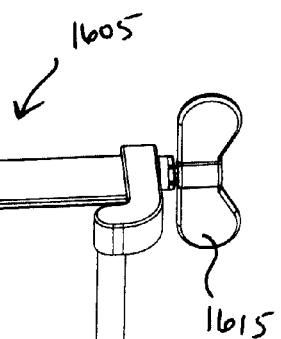
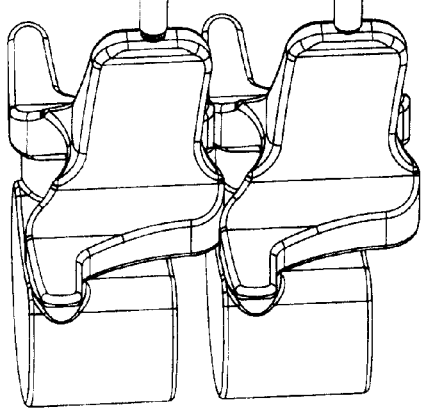
Figure 17

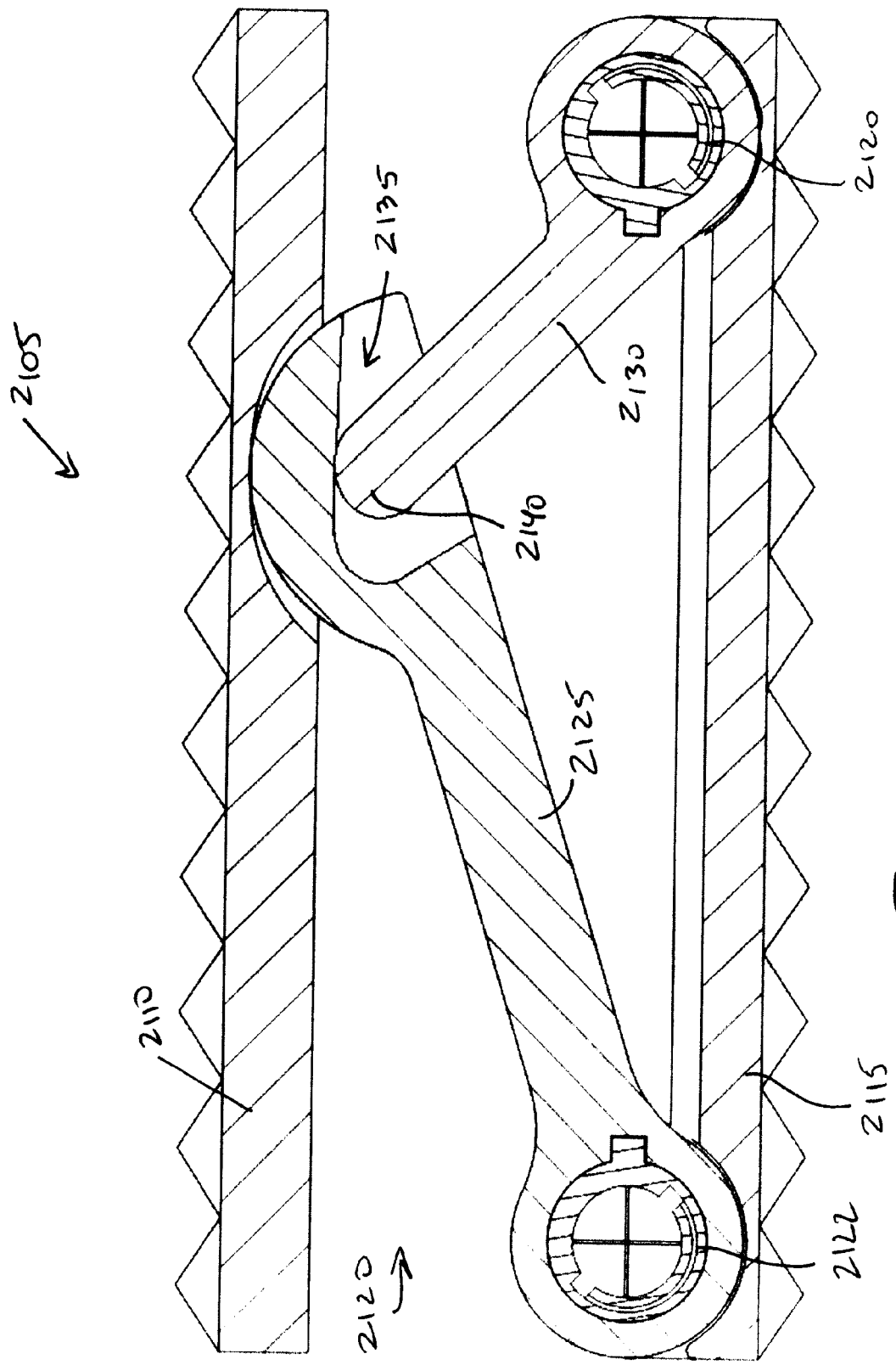

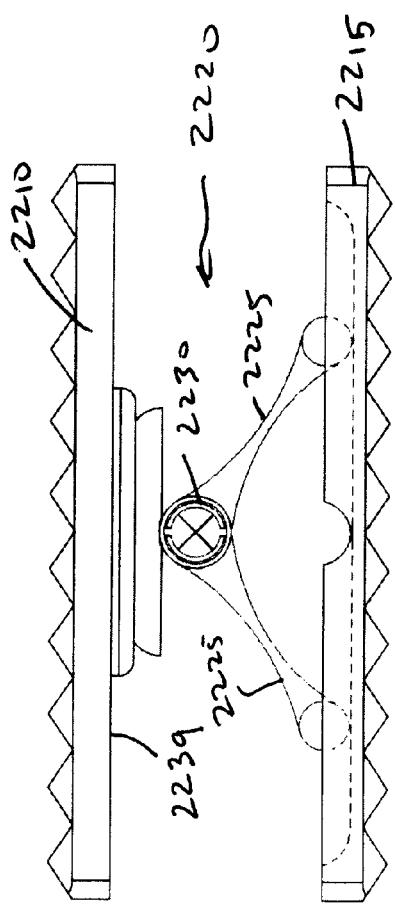
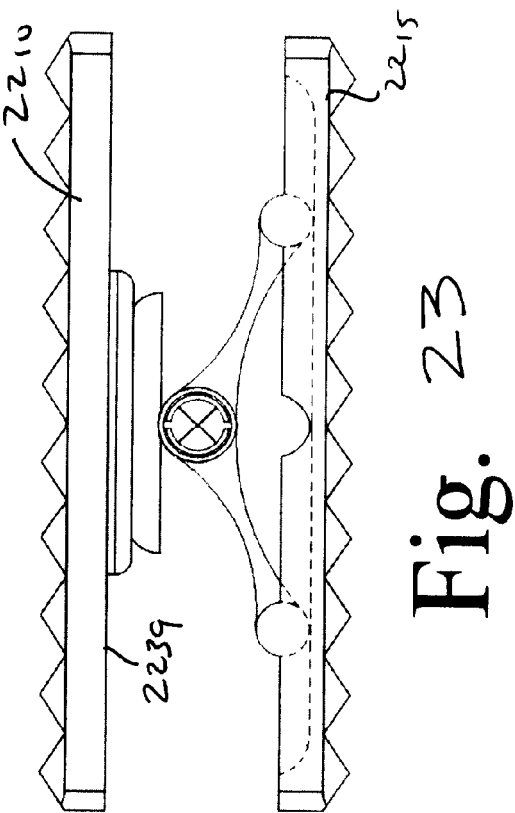

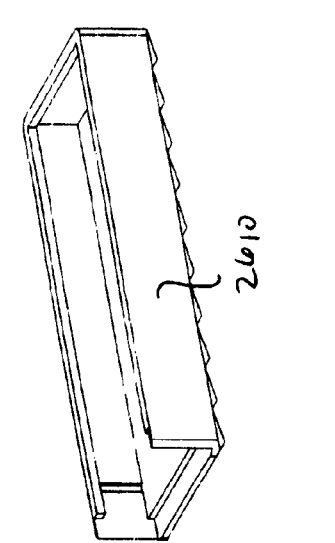
Fig. 26
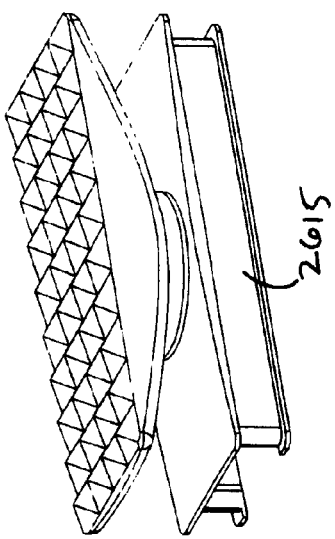
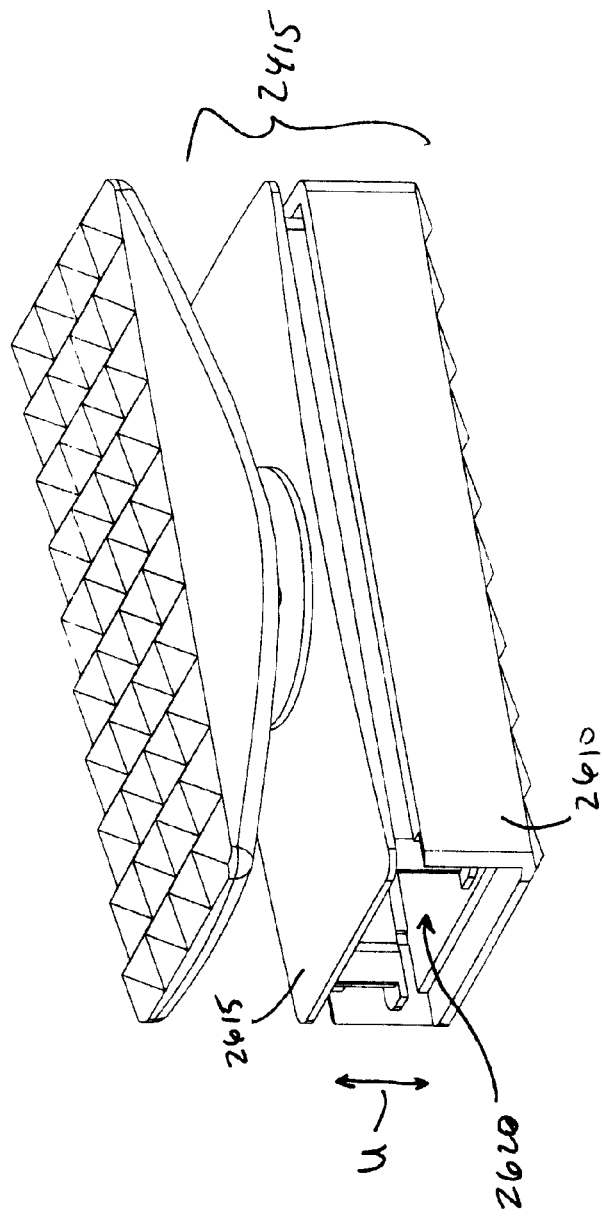
Fig. 27

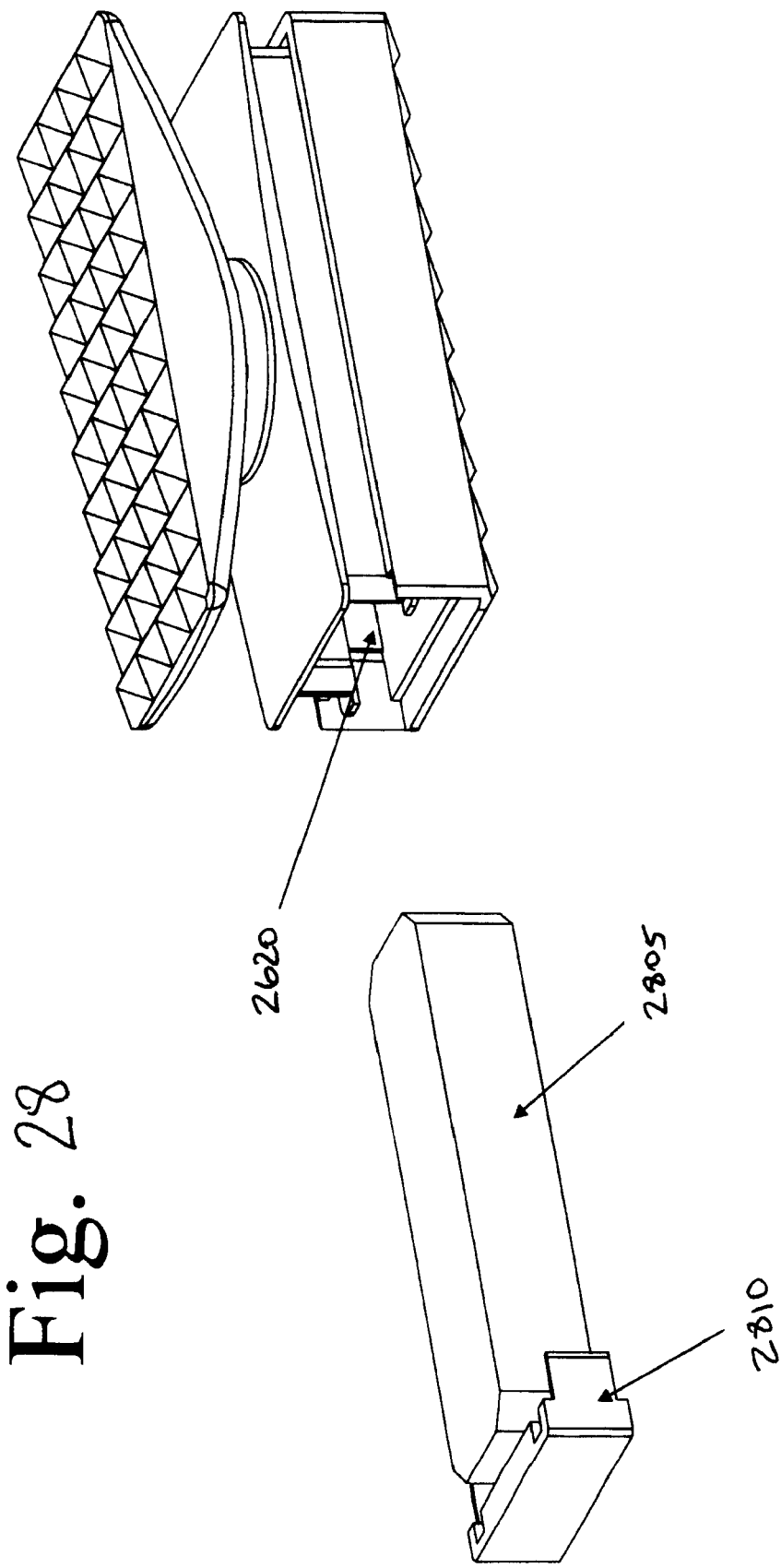

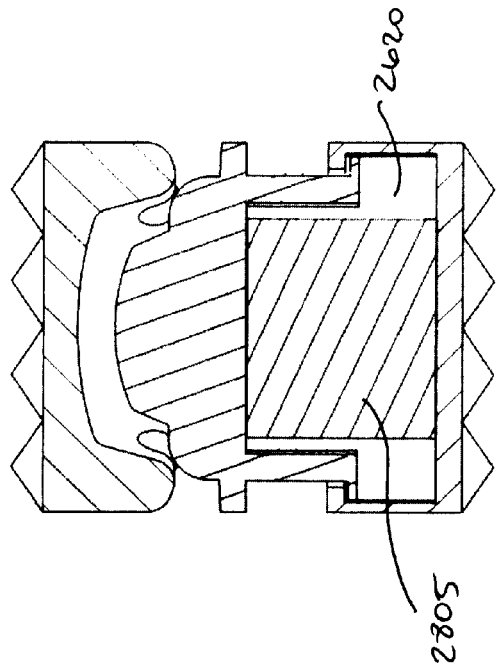
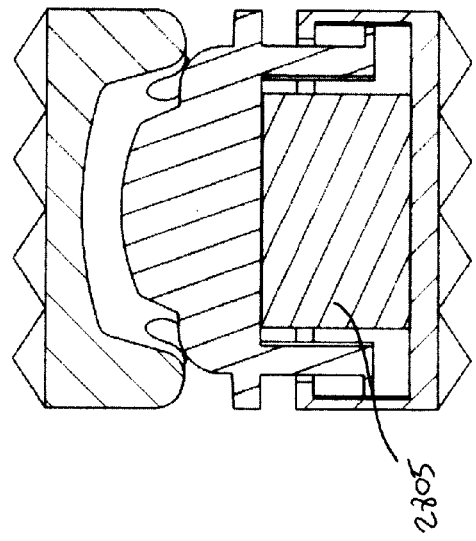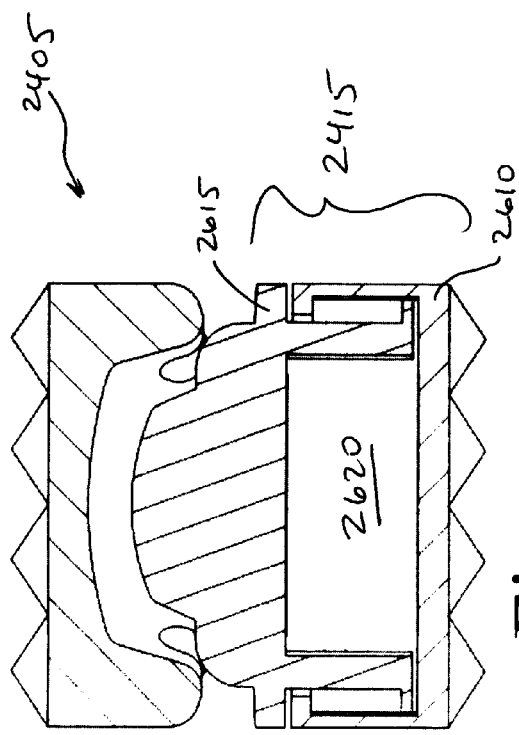

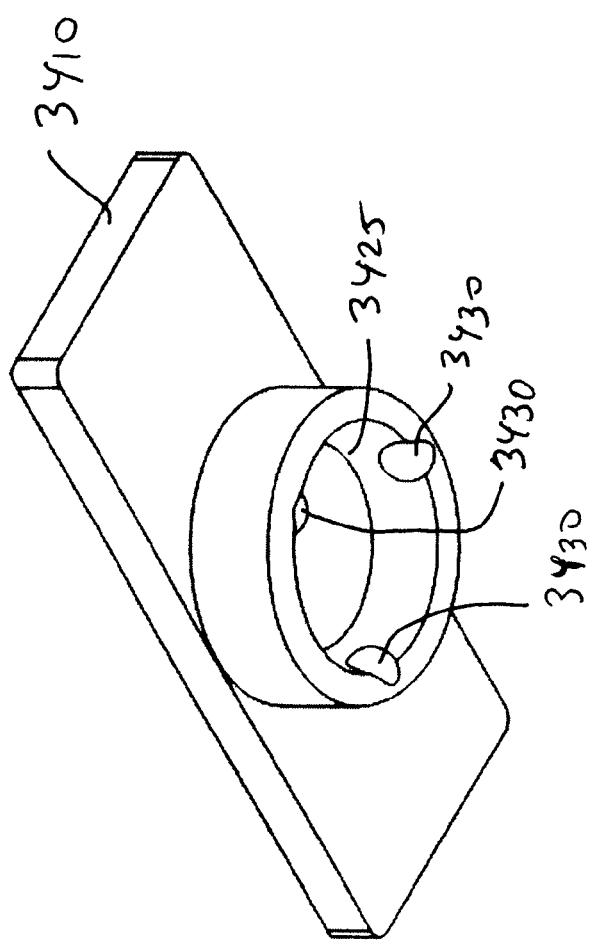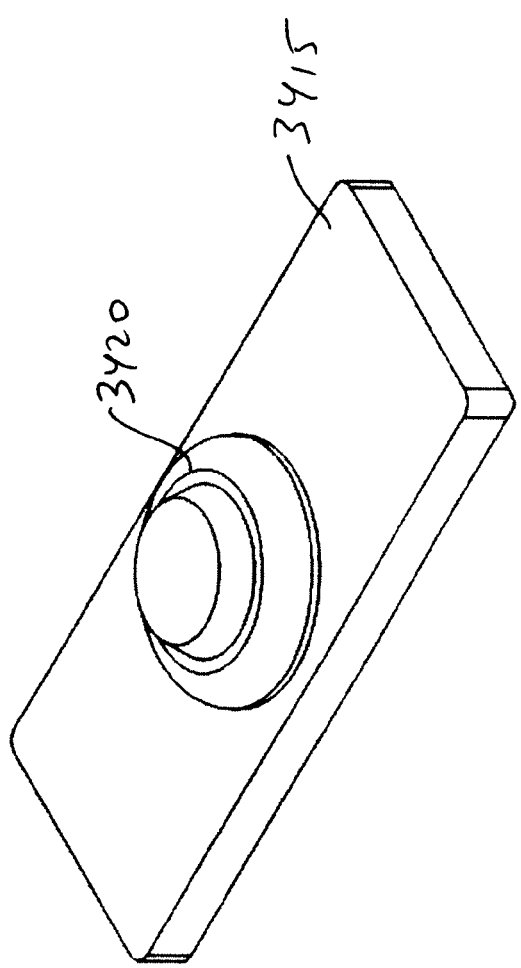
Figure 34

DEVICES AND METHODS FOR INTER-VERTEBRAL ORTHOPEDIC DEVICE PLACEMENT

REFERENCE TO PRIORITY DOCUMENT

This application claims priority of U.S. Provisional Patent Application Ser. No. 60/773,584 filed Feb. 15, 2006, U.S. Provisional Patent Application Ser. No. 60/850,473 filed Oct. 10, 2006, and U.S. Provisional Patent Application Ser. No. 60/874,195 filed Dec. 11, 2006. Priority of the aforementioned filing dates is hereby claimed and the disclosures of the Provisional Patent Applications are hereby incorporated by reference in their entirety.

BACKGROUND

The present disclosure relates to devices and methods that permit stabilization of the bony elements of the skeleton. The devices and methods permit adjustment and maintenance of the spatial relationship(s) between neighboring bones.

Spinal disease is a major health problem in the industrialized world and the surgical treatment of spinal pathology is an evolving discipline. The current surgical treatment of abnormal vertebral motion and low back pain is the complete immobilization and bony fusion of the involved spinal segment. An extensive array of surgical techniques and implantable devices has been formulated to accomplish this goal.

The growing experience with spinal fusion has shed light on the long-term consequences of vertebral immobilization. It is now accepted that fusion of a specific spinal level will increase the load on the spinal segments immediately above and below the fused level. Further, as a consequence of fusion, each adjacent disc will experience a displaced center of rotation and produce an aberrant motion profile. The increased load and abnormal movement experienced by the adjacent discs will synergistically act to accelerate the rate of degeneration at these levels. Consequently, the number of patients who require extension of their fusion to the adjacent, degenerating levels has increased with time. This second procedure necessitates re-dissection through the prior, scarred operative field and carries significantly greater risk than the initial procedure while providing a reduced probability of pain relief. Further, extension of the fusion will increase the load on the motion segments that now lie at either end of the fusion construct and will accelerate the rate of degeneration at those levels. Thus, spinal fusion begets additional, future fusion surgery.

There is a growing recognition that segmental spinal fusion and complete immobilization is an inadequate solution to degenerative disc disease. Replacement of the degenerated and painful disc with a mobile prosthesis is a more intuitive and rational treatment option. This approach preserves spinal mobility in a majority of spinal segments and reserves fusion and complete immobilization for those disc spaces where the degenerative disease is advanced and beyond surgical restoration.

U.S. Pat. Nos. 4,759,769; 4,997,432; 5,674,294; 5,674,296; 5,676,701; 5,888,226; 6,001,130; 6,019,792; 6,162,252; 6,348,071; 6,368,350; 6,419,706; 6,520,996; 6,540,785; 6,607,558; 6,645,249; 6,673,113; 6,749,635 and others have illustrated various artificial disc prosthesis. Despite the number of proposed designs, each device is sized to substantially occupy the majority of the disc space and replace the entire disc. Since the neural elements are anatomically positioned immediately posterior to the disc space, these large devices can be implanted only through an anterior or lateral surgical approach.

The spine is situated at the most posterior aspect of the body cavities and it can be most readily reached through a posterior approach. Anterior and lateral surgical approaches must dissect around and through the many vital organs and blood vessels that lie anterior to the spine and these approaches add to the risk and morbidity of the procedure. In addition, spine surgeons are more familiar with and technically versed in the posterior approach, further increasing the risks of the more difficult non-posterior approaches. Finally, the posterior approach allows the surgeon to advantageously remove the bone spurs that compress the neural elements at the same time they access the disc space.

The use of a posterior surgical approach to implant a mobile disc prosthesis has numerous advantages. Unfortunately, the intervening nerve elements limit the size of the posterior corridor that can be used to access the anterior disc space and a posteriorly-placed mobile disc prosthesis (i.e. "artificial disc") must be small enough to fit within that limited implantation corridor. Consequently, a posteriorly-placed artificial disc can only provide partial coverage of the disc space and partial replacement of the inter-vertebral disc. Attempts to overcome this problem by placing several implants within the disc space is limited by the significant difficulty in producing coordinated movement of separate implants about a specified center of rotation.

SUMMARY

In view of the preceding, there remains a need in the art for a prosthesis that can be safely placed into the disc space via a posterior surgical approach and used to replace the natural function of an inter-vertebral disc. Disclosed are devices and methods for the implantation of a mobile prosthesis within the disc space that can replace the function of a natural disc.

In one aspect, a prosthesis is comprised of an upper and lower abutment surfaces and an intervening malleable member. The device is sufficiently small so that implantation into an inter-vertebral disc space can be performed from a substantially posterior approach without significant impingement upon the neural elements.

In other aspects, the prosthesis contains two or more bearing members wherein one set of one or more bearing members provide rotational and/or translational movement between the upper and lower abutment surfaces of the prosthesis. A second set of bearing members allow the abutment surfaces to reversibly move towards one another so that the device is endowed with a shock-absorptive capability. The second set of bearing members also allow the device to be compressed into a secondary configuration of lesser volume so as to allow placement through a smaller implantation portal. Bearing surfaces of fixed and variable centers of rotation are illustrated.

In another aspect, there is disclosed a spinal implant device for the maintenance of relative motion between two adjacent vertebral bodies, comprising: a first member having an lower abutment surface adapted to contact an upper surface of a first vertebral body; a second member having an upper abutment surface adapted to contact a lower surface of a second vertebral body; and at least one malleable member between the first and second members that permits relative movement between the first and second members, wherein the device is adapted to be implanted within a disc space between the two vertebral bodies, and wherein the device is sufficiently small to be implanted into the disc space via a posterior approach to the disc space.

In another aspect, there is disclosed an orthopedic implant device for the maintenance of motion between two adjacent bones, comprising: a first member having an lower abutment surface adapted to contact an upper surface of a first bone; a second member having an upper abutment surface adapted to contact a lower surface of a second bone; and a coupler between the first and second members and movably attaching the first member to the second member, the coupler including (a) at least a first bearing mechanism comprising a first bearing surface that includes a malleable member that reversibly opposes a load on the implant so as to return the implant to a predetermined configuration after dissipation of the load; and (b) at least a second bearing mechanism comprising a second bearing surface adapted to permit the implant to permit motion between the first and second bones when positioned between the first and second bones.

In another aspect, there is disclosed a method for the placement of an orthopedic device within a disc space between two vertebral bodies, comprising: applying a distraction force to the two vertebral bodies to provide a corridor for the placement of the orthopedic device in the disc space between the two vertebral bodies, wherein a distractor device at least partially attaches to a spinous process or lamina of one of the vertebral bodies; and implanting the orthopedic device in the disc space using a substantially posterior placement corridor.

Placement methods are disclosed. In some placement protocols, vertebral distraction is incorporated in order to limit the necessity of bone and joint resection. In a novel application, the distractors are attachment the spinous processes or lamina of the adjacent vertebrae.

The implants described in this application can be safely placed into the disc space via a posterior surgical approach and used to replace the natural function of an inter-vertebral disc. Other features and advantages will be apparent from the following description of various embodiments, which illustrate, by way of example, the principles of the disclosed devices and methods.

BRIEF DESCRIPTION OF THE DRAWINGS

FIG. 2 shows various views of the implant of FIG. 1.

FIG. 9 shows a perspective view of another embodiment of an implant that is sized and shaped to be positioned within a disc space.

FIG. 10 shows various view of the implant of FIG. 9.

FIGS. 14 and 15 show perspective and side view of the implant positioned within a disc space between vertebral bodies V1 and V2.

FIG. 17 shows the distractor device coupled to the distractor screws.

FIG. 18 shows the vertebral bodies after being distracted such that the disc space is accessible.

FIG. 21 shows another embodiment of an implant.

FIGS. 22 and 23 show another embodiment of an implant.

FIGS. 26 and 27 show partially exploded views of the implant of FIG. 25.

FIG. 28 shows another exploded view of the implant.

FIG. 29 shows the implant in a compressed state.

FIG. 30 shows the implant with a malleable member positioned in an internal cavity.

FIG. 31 shows the implant under load.

FIG. 34 shows another embodiment of an implant.

DETAILED DESCRIPTION

Disclosed are devices and methods for the implantation of a mobile prosthesis within the disc space between two vertebrae. The mobile prosthesis is adapted to replace the function of a natural disc. Various implants are described herein.

Figure 1:
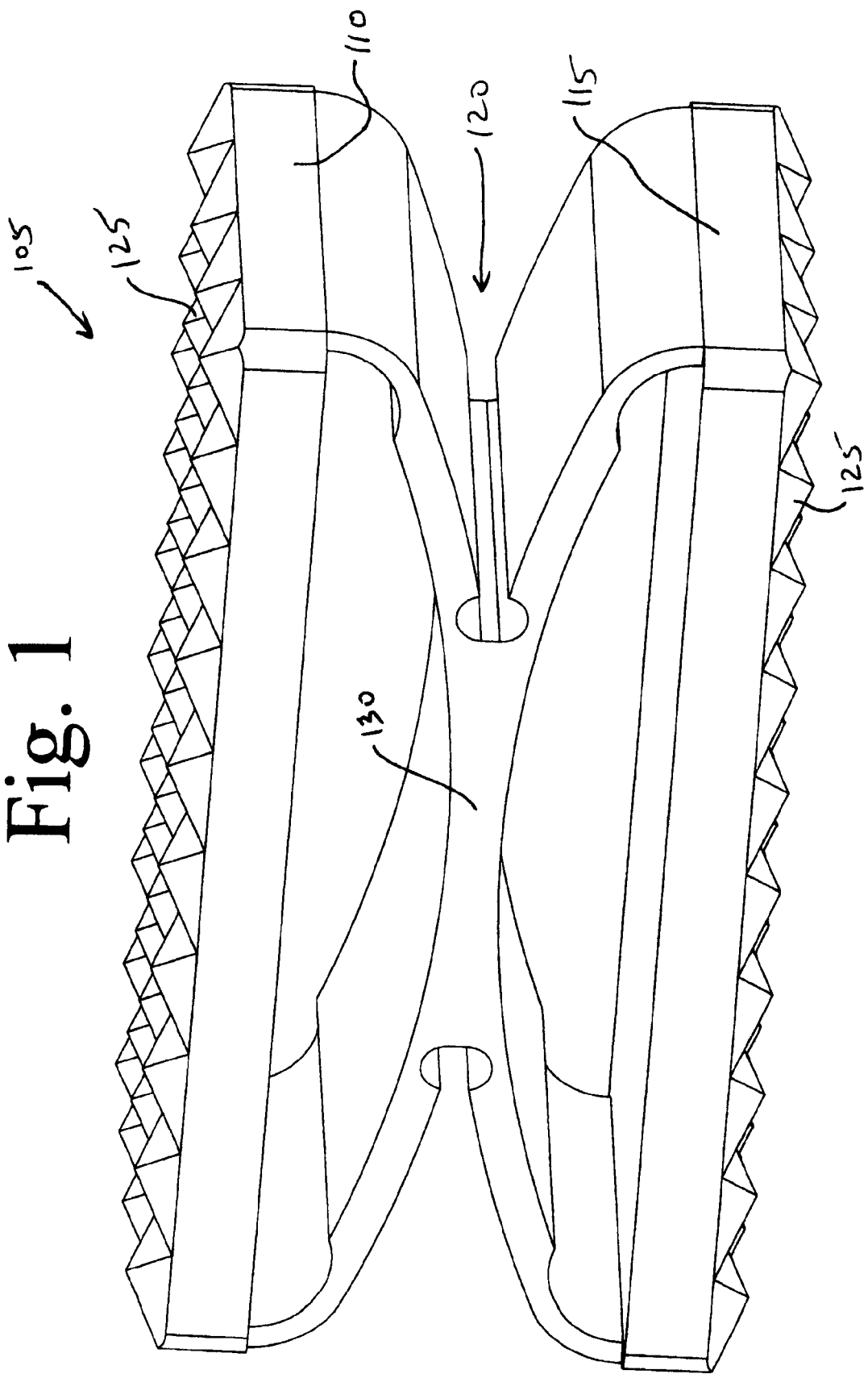
FIG. 1 shows a perspective view of implant 105 that is sized and shaped to be positioned within a disc space.

FIG. 1 shows a perspective view of a first embodiment of an implant 105 that is sized and shaped to be positioned within a disc space between a pair of vertebrae in a spine. FIG. 2 shows various views of the implant of FIG. 1. The implant 105 includes an upper component 110 and a lower component 115. An elastic middle component 120 is interposed between the upper and lower components. It should be appreciated that the terms "upper" and "lower" are for reference purposes and use of such terms should not be limiting with respect to placement orientation.

The middle component 120 is adapted to deform or change shape in response to loads on the upper and/or lower components. The middle component 120 is elastic and biased toward a default shape such that the implant returns to an initial configuration or shape after the force acting upon the implant has dissipated. In this regard, the middle component 120 has a leaf spring-like configuration that is formed, for example, of a pair of inclined walls that meet at a connection location 130. The walls can flex about the connection location to permit the middle component 120 to change shape while being biased toward the default shape.

The middle component 120 is depicted in FIG. 1 as a spring-like member such that the structural shape of the middle component provides spring-like qualities. The middle component 120 can be alternatively or in combination made of any visco-elastic material(s) such as to compliment or enhance the spring-like qualities of the middle component 120. Further, the middle component 120 can be fluid based and resist motion by the use of hydrodynamic forces or it can employ magnetic fields that repel/attract various implant components and produce the desired motion characteristics.

Middle compartment 120 may be at least partially made of shape memory materials that exhibit a stress-induced martensitic transformation. Shape memory materials plastically deform from a first configuration into a second configuration and then return to the first "memorized" configuration in response to a stimulus. The ability of the material to reversibly change shape is secondary to a phase transformation so that the material essentially exists in either an austenitic state or a martensitic state. A phase shift secondary to a temperature change is called a thermoplastic martensitic phase transformation while a shift due to the imposition of load is termed a stress-induced martensitic transformation. Shape-memory materials include a number of shape-memory alloys and shape-memory polymers. The former include a variety of alloys of known metals such as, for example, nickel and titanium, copper and zinc as well as copper, aluminum and nickel. Shape memory polymers have also been described and usually consist of a plastic polymer with two or more components that have different thermal characteristics. These components include, for example, oligo (e-caprolactone) diol and oligo (p-dioxanone) diol. Additional materials exist that reversibly alter shape in reaction to PH, moisture and magnetic and electrical fields. Shape memory alloys that respond to a load change are particularly suitable for this application.

Figure 39:
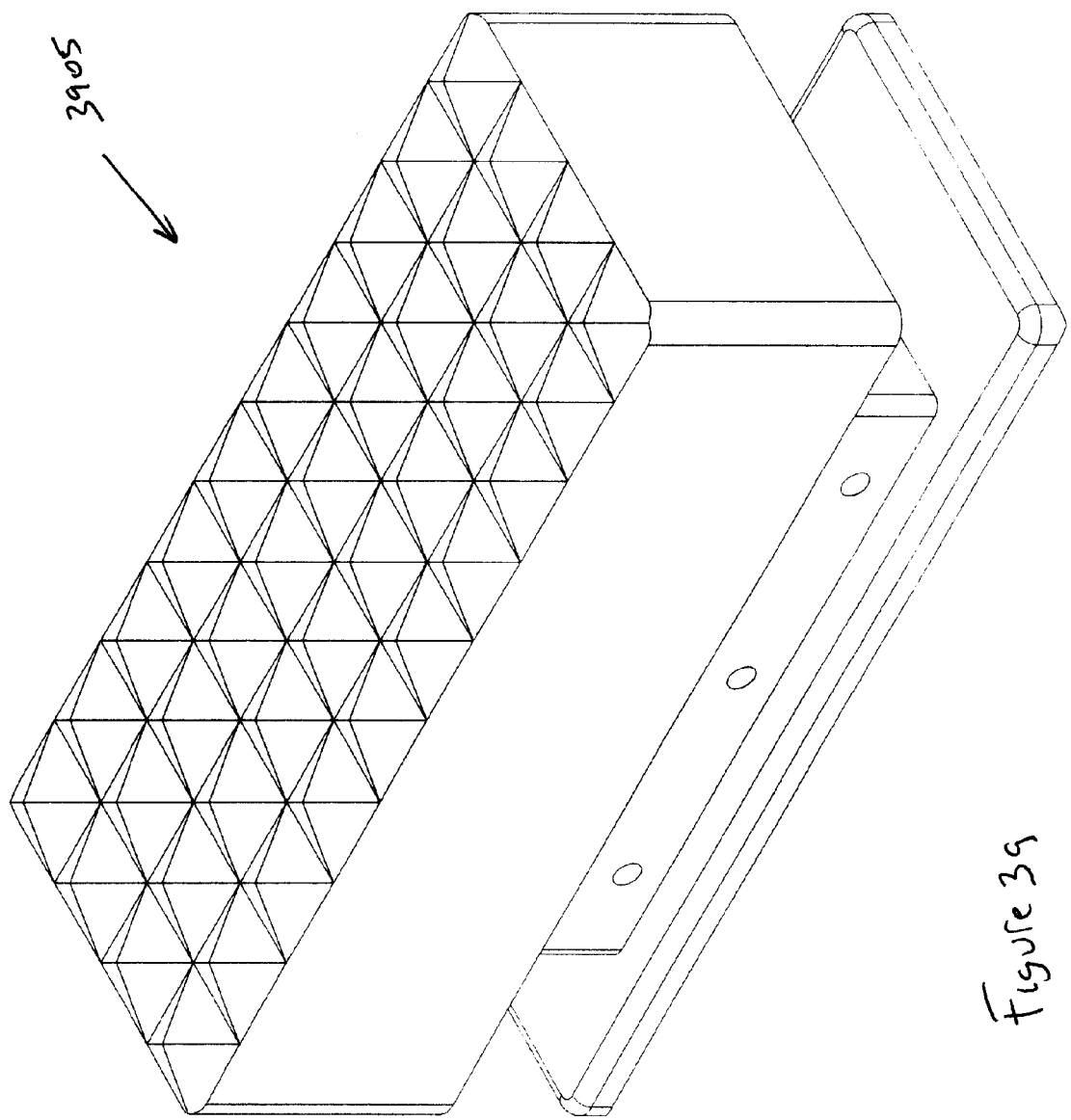
FIGS. 39-42 show another embodiment of an implant.

The upper and lower components 110 and 115 each have an abutment surface 125 that is adapted to abut against a vertebra when the implant 105 is positioned in a disc space. The abutment surfaces 125 of the upper and lower components are preferably configured to promote interaction with the adjacent bone and affix the implant to the bone. While depicted as having pyramidal protrusions, the abutment surfaces may have any of a variety of configurations for promoting such interaction. For example, the abutment surfaces may be alternatively textured, corrugated or serrated. The surfaces may be also coated with substances that promote osteo-integration such as titanium wire mesh, plasma-sprayed titanium, tantalum, and porous CoCr. The surfaces may be further coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, helical rosette carbon nanotubes or other carbon nanotube-based coating may be applied to the surfaces to promote implant-bone interaction. Lastly, a portion of components 110 and 115 could be also incorporated with bone fragment or a bone graft substitute (as illustrated in the embodiment of FIG. 39) to fuse onto the vertebral surfaces.

Figure 4:
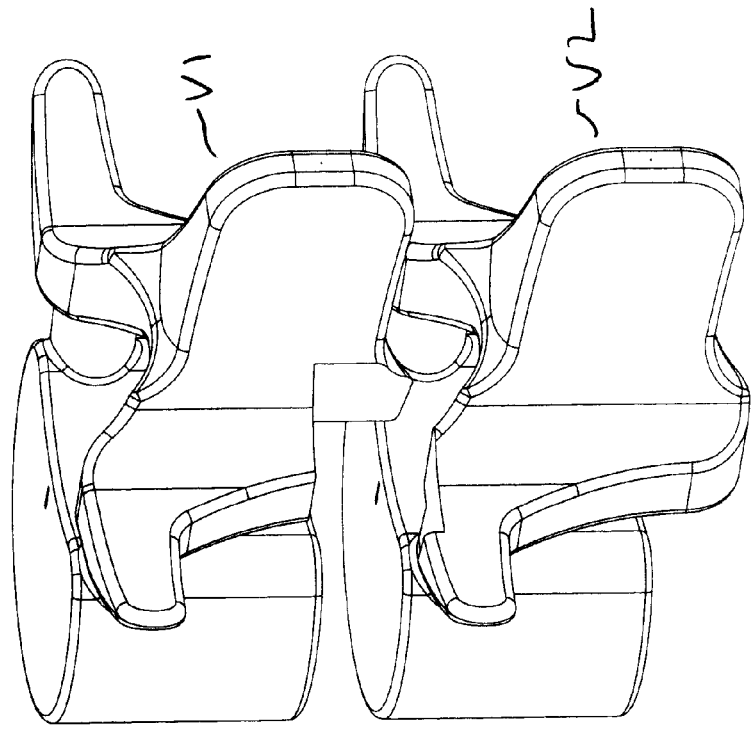
FIG. 4 shows the spinal motion segment after a surgical procedure wherein the left facet joint of vertebral body V1 has been removed.
Figure 3:
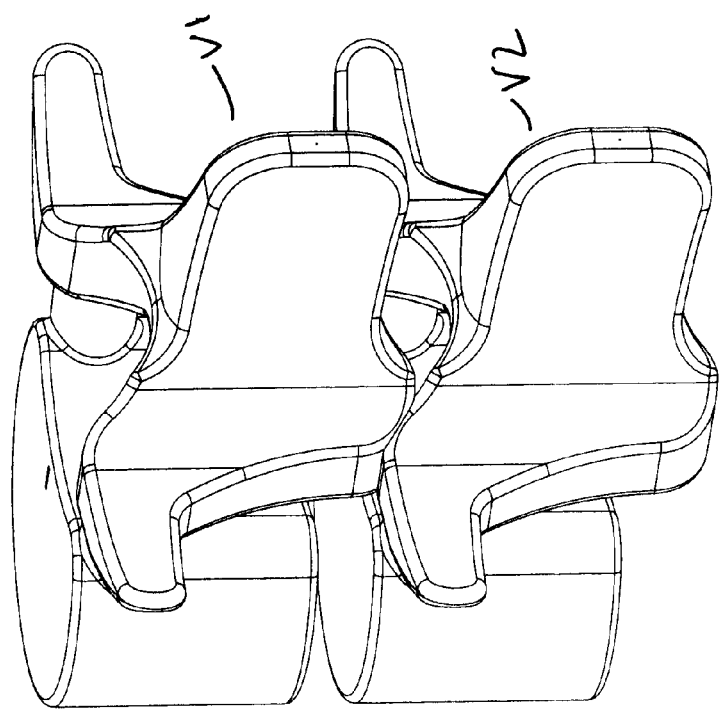
FIG. 3 shows a spinal motion segment composed of two adjacent vertebral bodies V1 and V2 and the intervening disc space.

A method of positioning or implanting the implant 105 is now described. FIG. 3 shows a spinal motion segment composed of two adjacent vertebral bodies V1 and V2 and the intervening disc space. For clarity of illustration, certain anatomical details are not shown in FIG. 3 or the accompanying figures. Preferably, a portion of at least one of the vertebrae is removed in order to facilitate device placement. FIG. 4 shows the spinal motion wherein at least a segment of the left facet joint of vertebra V1 & V2 is removed thereby forming a pathway for implantation of the implant 105 into the disc space.

Figure 6:
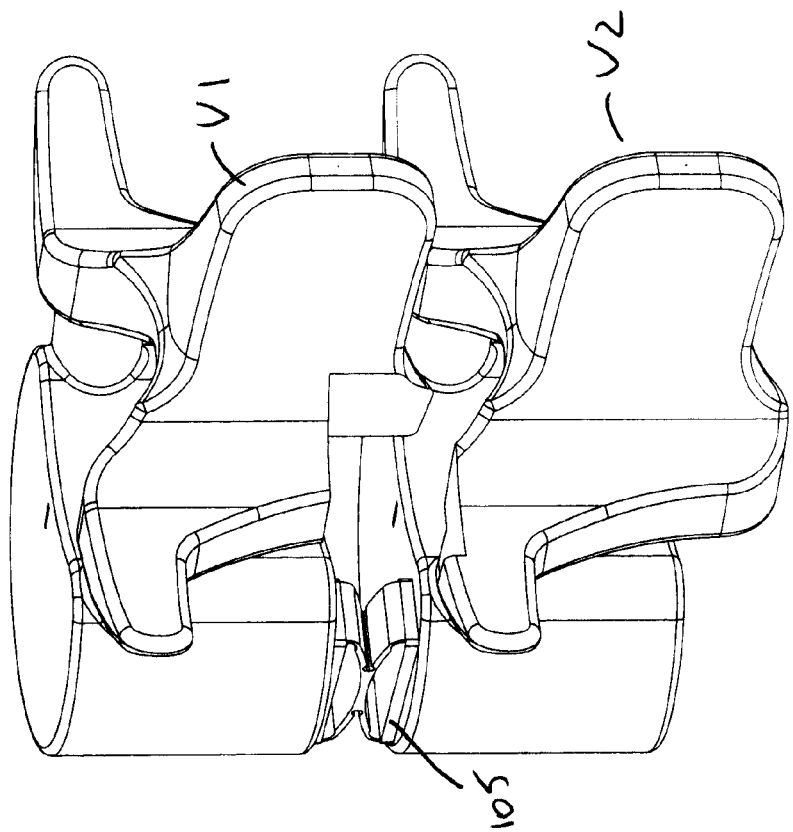
FIG. 6 shows the implant positioned within the disc space between the vertebral bodies V1 and V2.
Figure 5:
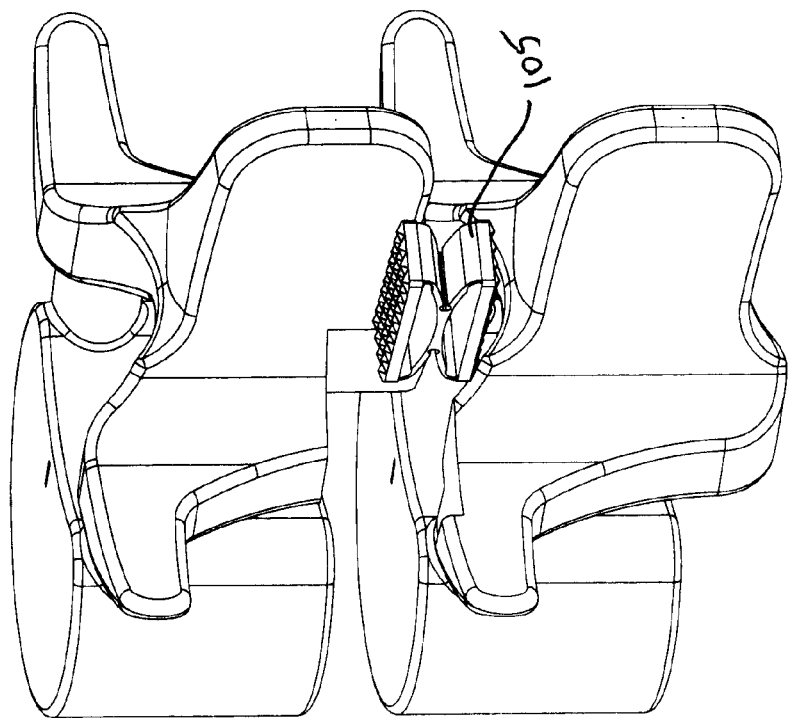
FIG. 5 shows the implant positioned adjacent the disc space.
Figure 8:
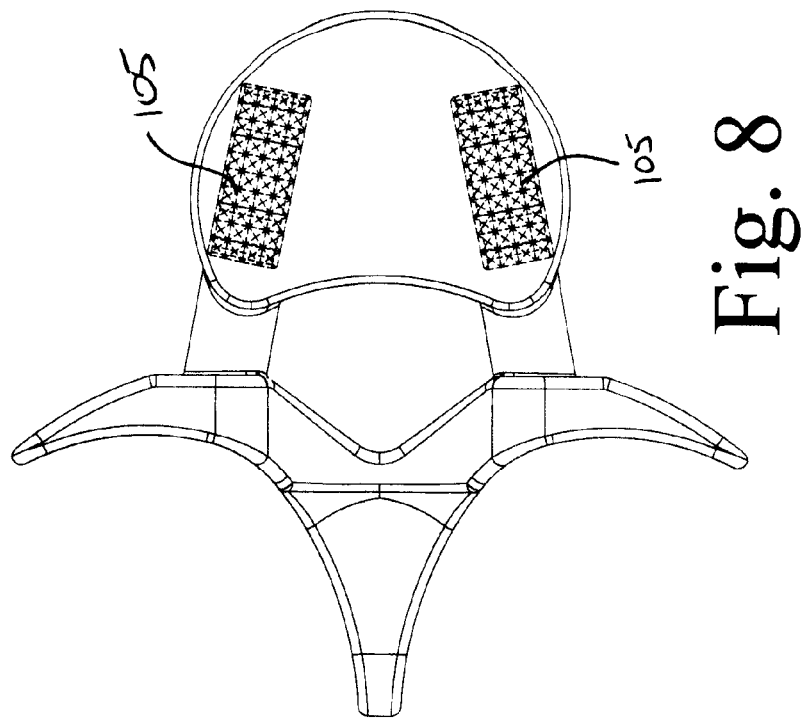
FIG. 8 shows a spine axial view of a pair of implant positioned in the disc space on either side of the spinal midline.
Figure 7:
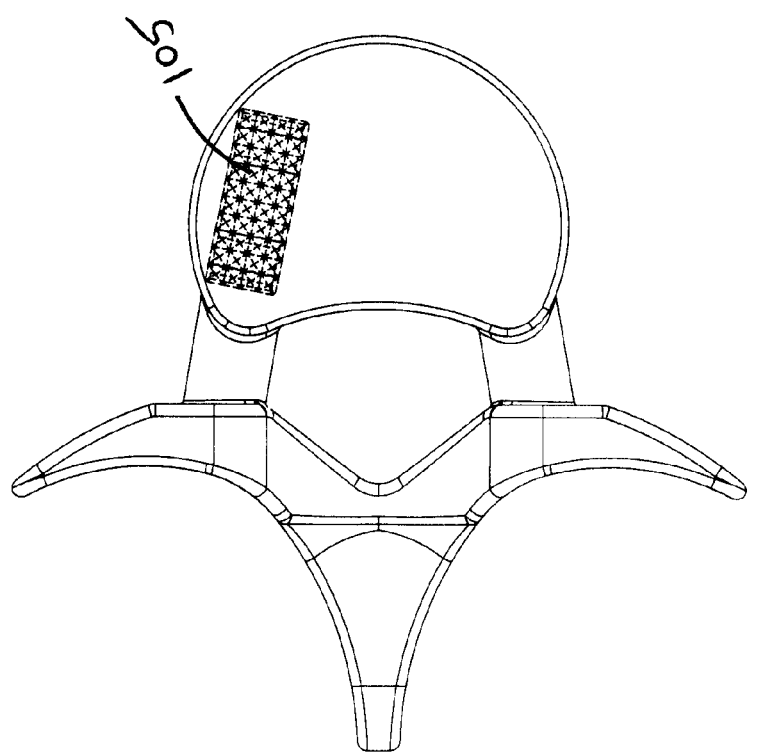
FIG. 7 shows a spine axial view of the implant positioned in the disc space.

Next, the implant 105 is positioned for implantation into the disc space, as shown in FIG. 5. FIG. 5 shows the implant 105 positioned adjacent the disc space. The implant 105 is positioned such that the abutment surfaces can be positioned adjacent the bone. FIG. 6 shows the implant 105 positioned within the disc space between the vertebral bodies V1 and V2. The abutment surfaces of the upper and lower components of the implant are positioned to contact the bone. FIG. 7 shows an axial view of the implant positioned in the disc space. In another embodiment, the procedure is performed bilaterally so that at least one implant 105 is placed on each side of the spinal midline as shown in FIG. 8.

Figure 11:
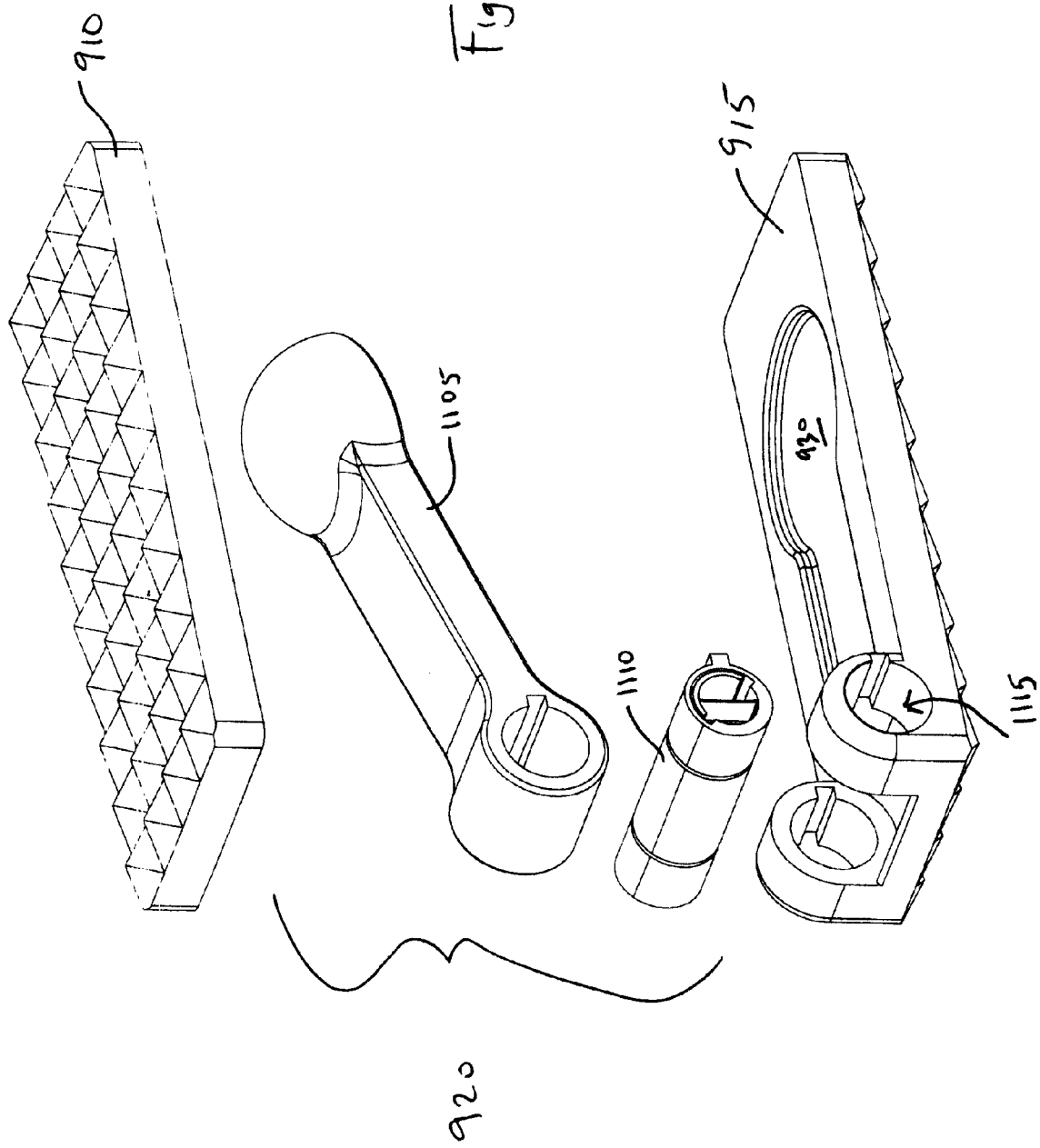
FIG. 11 shows the implant in an exploded state.

FIG. 9 shows a perspective view of another embodiment of an implant 905 that is sized and shaped to be positioned within a disc space. FIG. 10 shows various view of the implant 905. FIG. 11 shows the implant 905 in an exploded state. The implant 905 includes an upper component 910, a lower component 915, and a middle component 920. As in the previous embodiment, the upper and lower components each have an abutment surface 925 that is adapted to abut against a vertebra when the implant 905 is positioned in a disc space. The abutment surfaces 925 of the upper and lower components are preferably configured to promote interaction with the adjacent bone and affix the implant to the bone. The lower component 915 has an interior surface with a cavity or seat 930 that is sized to receive at least a portion of the middle component, as described below.

The middle component 920 is adapted to deform or otherwise yield in response to loads on the upper and/or lower components. In this regard, the middle component is biased toward a default shape or position such that the implant returns to an initial configuration or shape after the force acting upon the implant has dissipated. With reference to the exploded view of FIG. 11, the middle component 920 includes a lever member 1105 that is pivotably coupled about a hinge member 1110. The hinge member 1110 mounts within a shaft 1115 in the lower component 915. The lever can be at least a first bearing mechanism comprising a first bearing surface that includes a malleable member that reversibly opposes a load on the implant so as to return the implant to a predetermined configuration after dissipation of the load.

Figure 12:
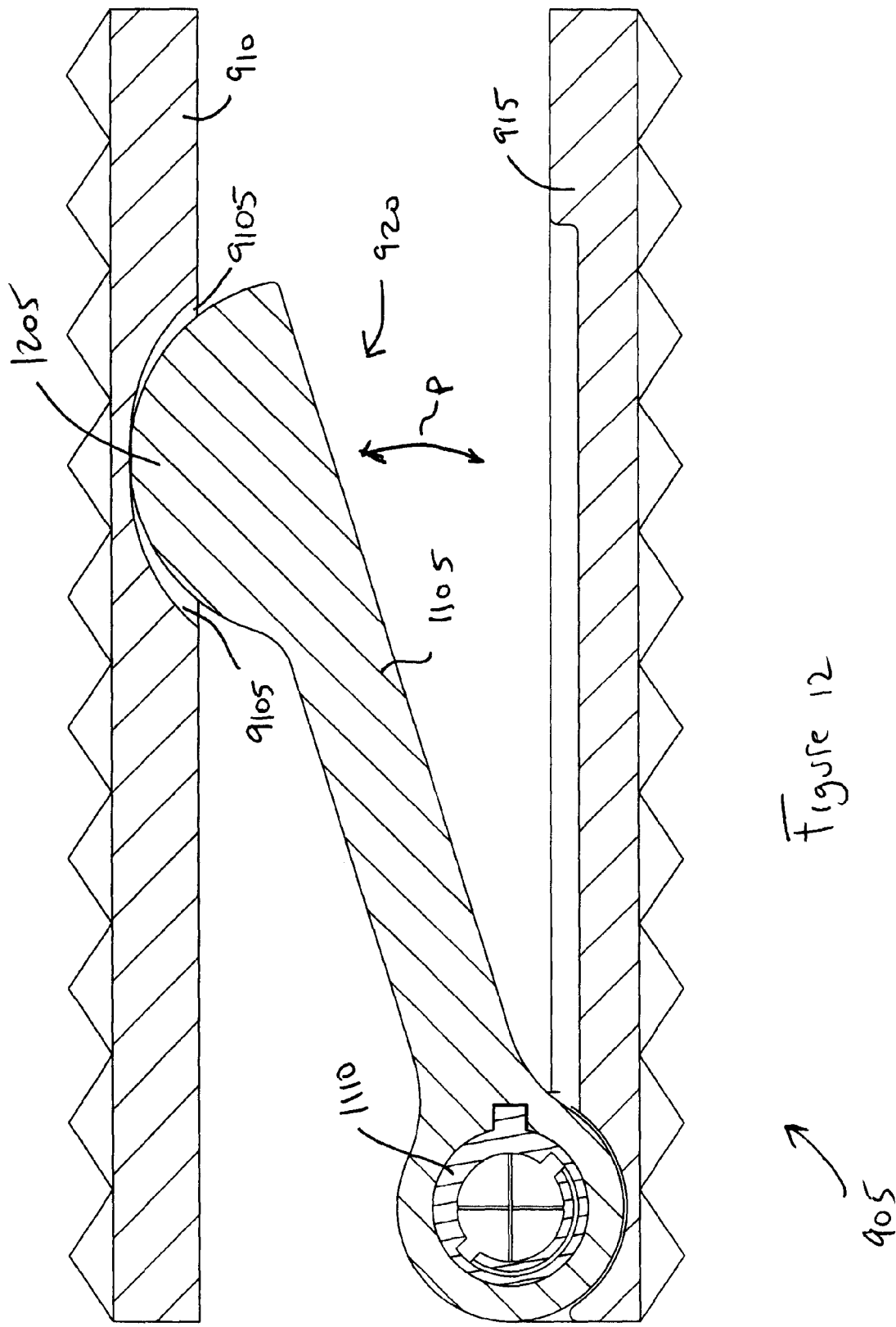
FIG. 12 shows a side cross-sectional view of the implant.

FIG. 12 shows a side cross-sectional view of the implant 905. The lever member 1105 includes a head 1205 that abuts into a seat in an interior surface of the upper component 910. In a default state, the lever member 1105 is biased toward the position shown in FIG. 12. The lever member 1105 is adapted to pivot about an axis defined by the hinge member 1110 such that the lever member 1105 can move about a curvilinear pathway, as represented by the arrow P in FIG. 12. In this manner, the lever member 1105 can change position in response to loads on the implant 905 such that the upper and lower components can move toward one another in a manner that is limited by movement of the lever member 1105.

Figure 13:
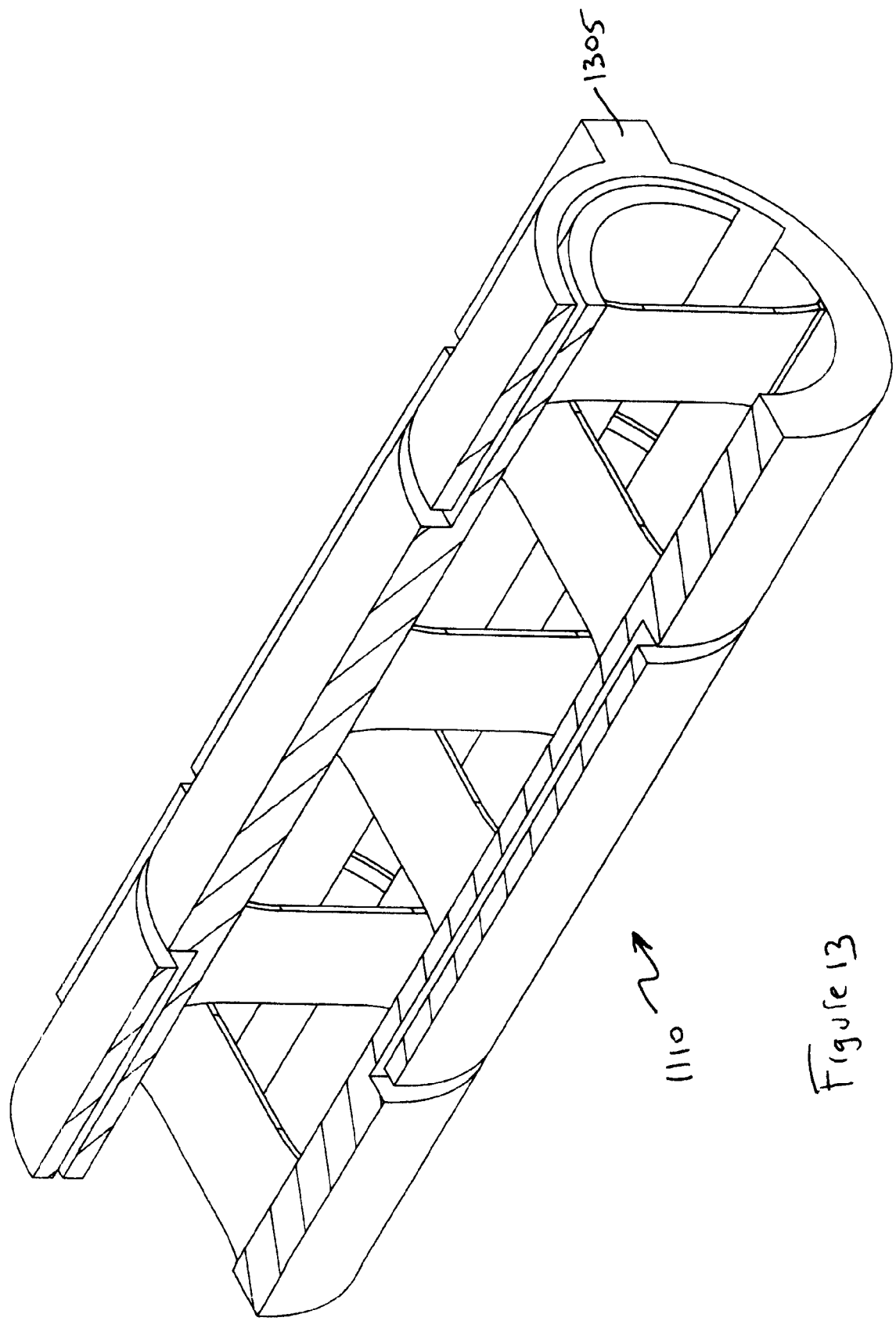
FIG. 13 shows a perspective view of the hinge member of the implant.

The lever member 1105 is coupled to the hinge member 1110, which is adapted to deform or articulate in response to loads thereon. FIG. 13 shows a perspective view of the hinge member of the implant 905 with a wall segment removed. The hinge member 110 includes an outwardly extending tooth 1305 that mates with complimentary-shaped slot in the lever member 1105. The hinge member 1110 is formed of a plurality of sections. The hinge member is a flexure based bearing, utilizing internal flat crossed springs, capsuled in a cylindrical housing, to provide precise rotation with low hysteresis and little frictional losses. The bearing is relatively friction-free, requires no lubrication, and is self-returning. The hinge member can resist rotational movement away from a neutral state and the extent of resistance to rotation is directly related to the extent of rotation. The extent of resistance to rotation can be a pre-determined property of the device. In one embodiment, the hinge member has high radial stiffness, high axial stiffness and is frictionless (hence, no particle wear debris). An exemplary hinge member of the type shown in Figure is distributed by Riverhawk Company of New York under the name FREE FLEX PIVOT.

A second bearing surface is provided by the spherical head 1205 of member 1105 and complimentary cut out 9105 of component 910. The interaction forms a ball-and-socket type joint. Cut-out 9105 is preferably of slightly larger diameter than head 1205 so that the articulation forms a loose-fitting joint and permits additional translational movement between the components. Bore holes 9110 (FIG. 10) are preferably threaded and permit the device to interact with a placement instrument. The latter can also function to compress the device during implantation. The spherical head can be a second bearing mechanism comprising a second bearing surface adapted to permit the implant to permit motion between the first and second bones when positioned between first and second bones.

FIGS. 14 and 15 show perspective and side view of the implant 905 positioned within a disc space between vertebral bodies V1 and V2. The implant 905 is positioned such that the abutment surfaces of the upper and lower components abut the adjacent bone within the disc space. The lever member 1105 can pivotably move in the manner discussed above in response to loads on the vertebral bodies.

Figure 16:
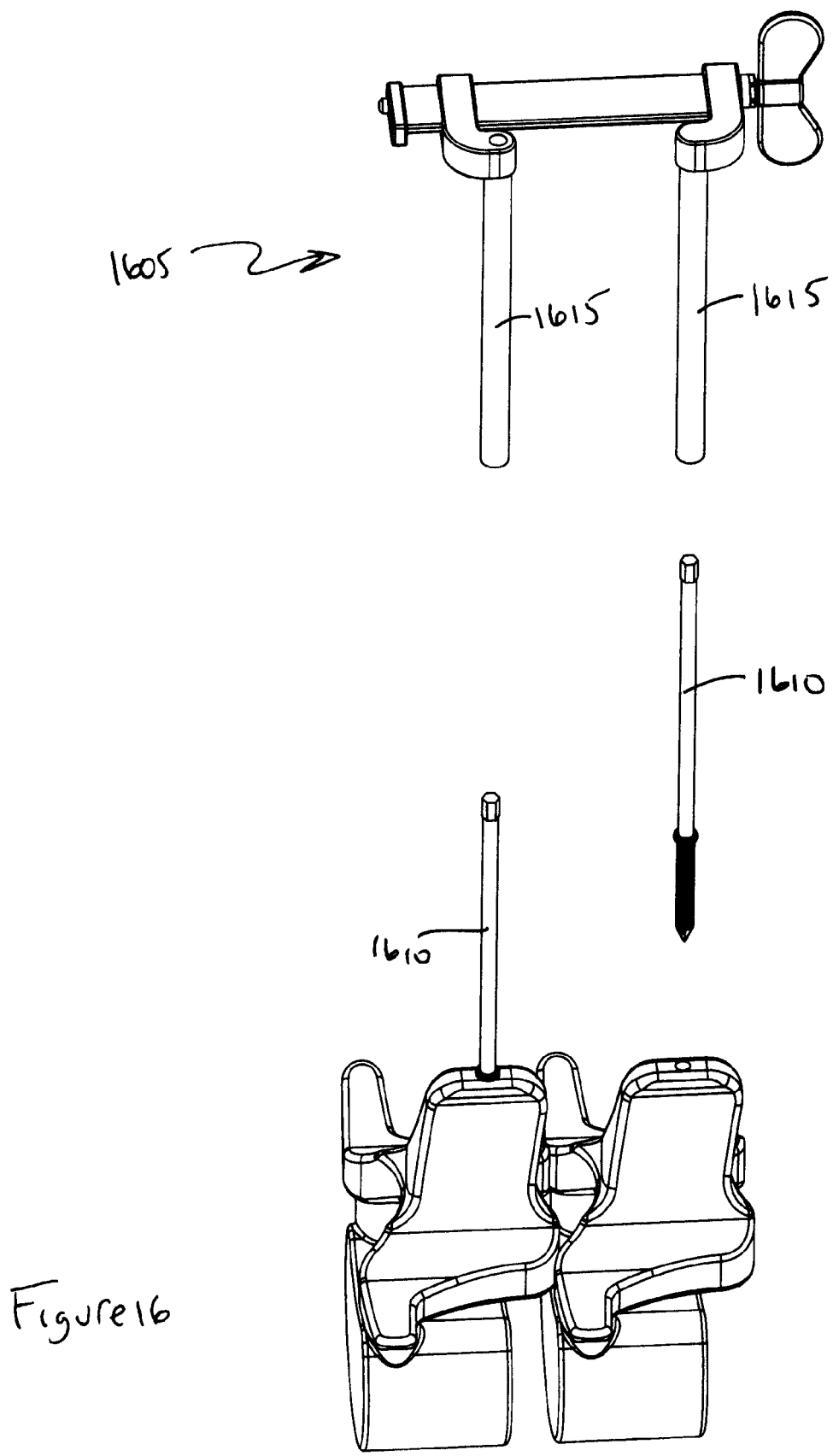
FIG. 16 shows an exemplary distractor device that couples to a pair of distractor screws.

While the current embodiment may be implanted using a placement procedure similar to that of the first embodiment, alternative placement protocols may be also used. An exemplary method of implant 905 placement is now described. In an initial step, a distractor device is coupled to the vertebral bodies for distracting the vertebral bodies. FIG. 16 shows an exemplary distractor device 1605 that couples to a pair of distractor screws 1610. The distractor screws 1610 are fastened onto the vertebral bodies such that they extend outwardly therefrom. The distractor device 1605 includes a pair of sheaths 1615 that are configured to couple to the distractor screws 1610, such as by sliding over the distractor screws. FIG. 17 shows the distractor device 1605 coupled to the distractor screws 1610. The distractor device 1605 includes an actuator 1615 that can be actuated to exert a distraction force onto the vertebral bodies such that the vertebral bodies are distracted. FIG. 18 shows the vertebral bodies after being distraction such that the disc space is accessible.

Figure 19:
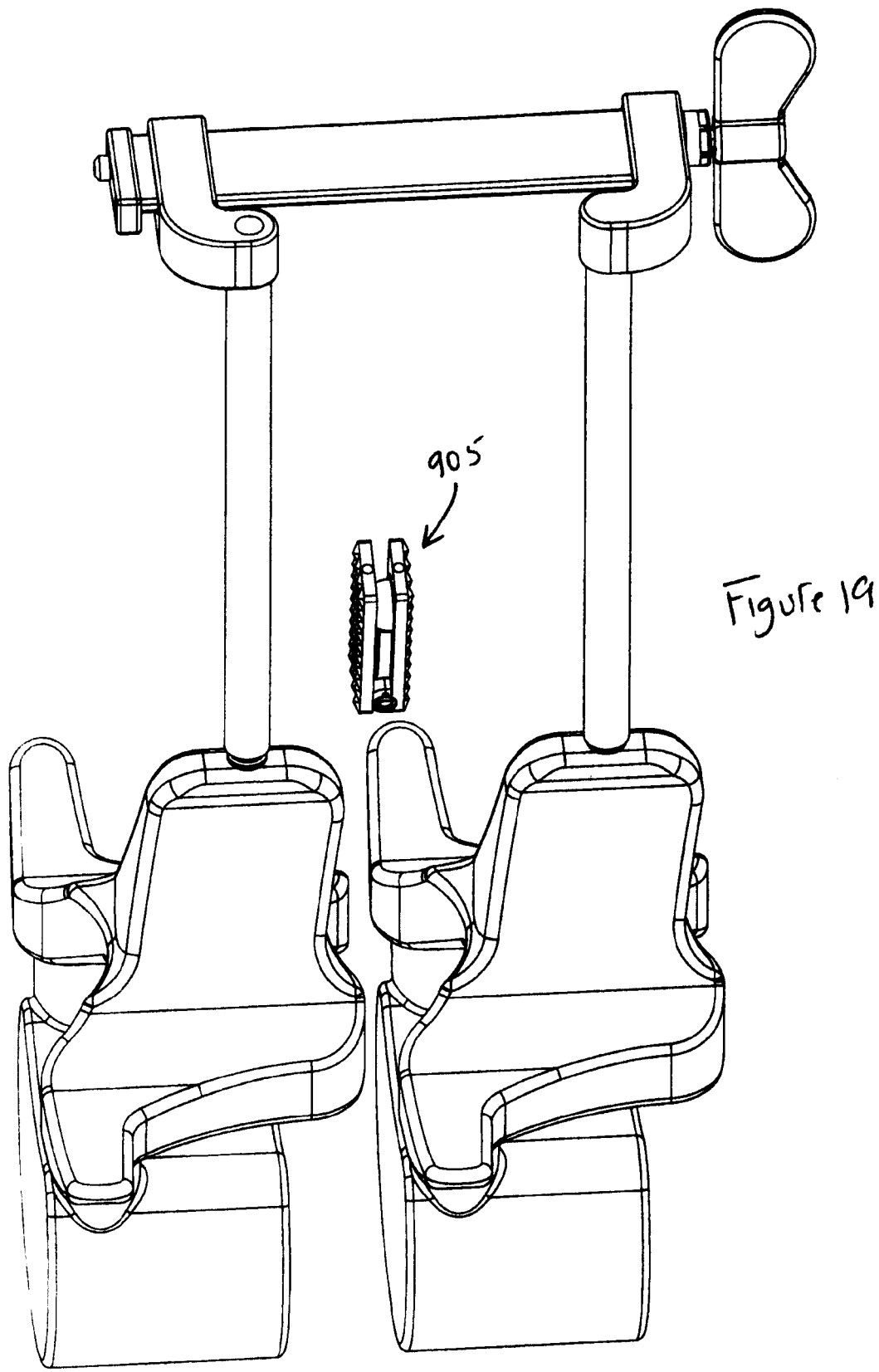
FIG. 19 shows the implant adjacent the disc space prior to implantation into the disc space. The implant is transitioned into a compact configuration.

FIG. 19 shows the implant 905 adjacent the disc space prior to implantation into the disc space. During the implantation procedure, the implant 905 can be in a compressed state of reduced size. When in this state, the upper and lower components are compressed toward one another such that the lever member 1105 is sitting within the seats on the interior surface of the upper and lower components. Thus, the implant 905 has a reduced sized profile when in the compressed state. As discussed, the implant 905 is biased toward the uncompressed state shown in FIG. 12. Once the implant 905 is positioned within the disc space, the implant 905 will tend to move toward the uncompressed state as limited by the interaction with the vertebral bodies.

Figure 20A:
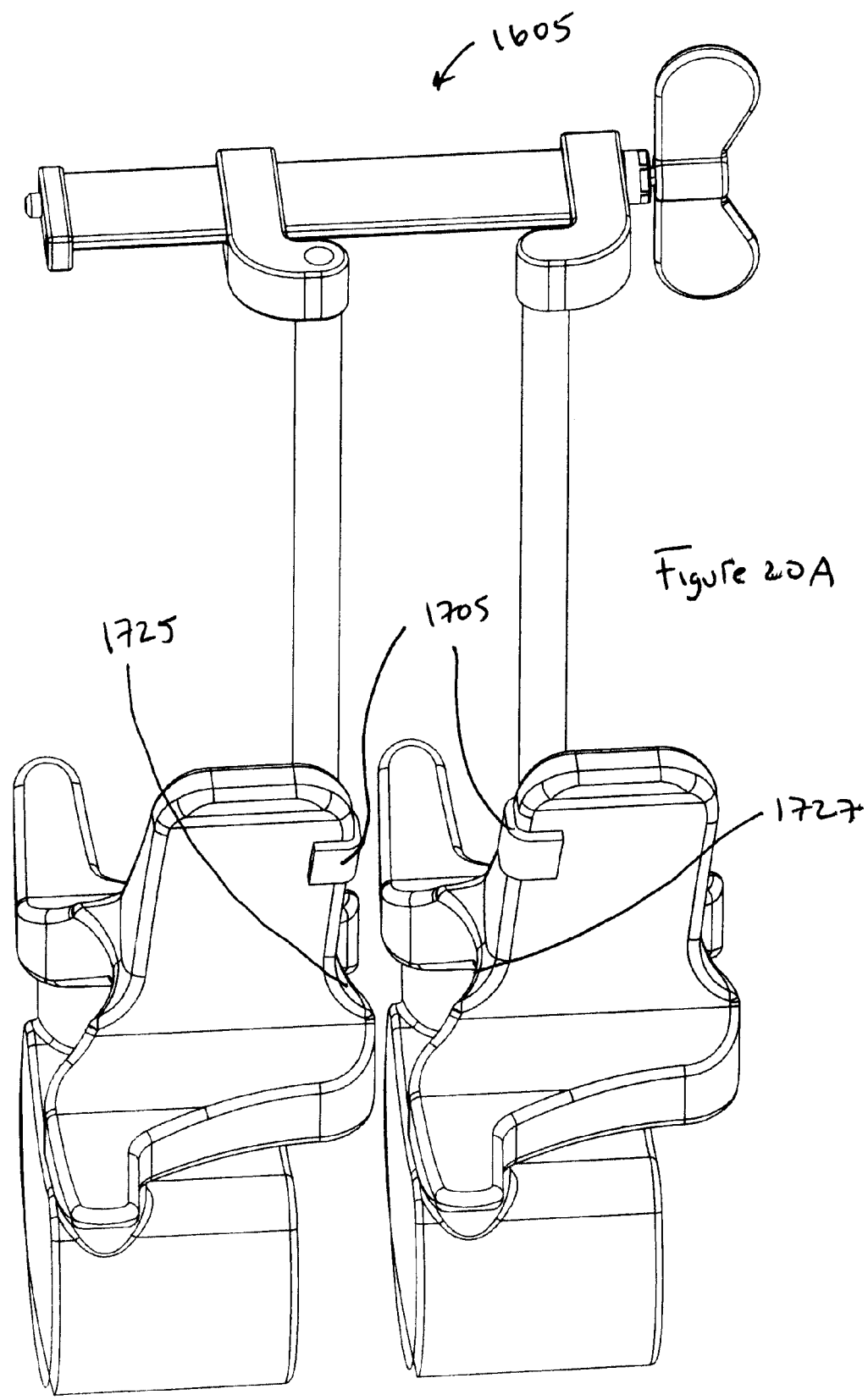
FIG. 20A shows an embodiment of a distractor device that does not utilize distraction screws to engage the vertebrae.

During implantation, the decrease in implant size by folding and the increase in the placement corridor by vertebral distraction will advantageously permit device placement without significant removal of the facet joint and other bony elements. It should be appreciated that the manner in which the vertebral bodies are distracted can vary. For example, FIG. 20A shows an embodiment of a distractor device 1605 that does not utilize distraction screws that fasten onto the spinous processes of the vertebrae. Rather, the distractor device 1605 includes a pair of clips 1705 that are each shaped to rest against a portion of a spinous process. Alternatively, a distractor with clip-like attachments similar to 1705 may be positioned against the lower edge 1725 of the upper lamina (FIG. 20A) and the upper edge 1727 of the lower lamina (FIG. 20A) and used to distract the vertebrae. Any other means of vertebral distraction can also be used.

Figure 20C:
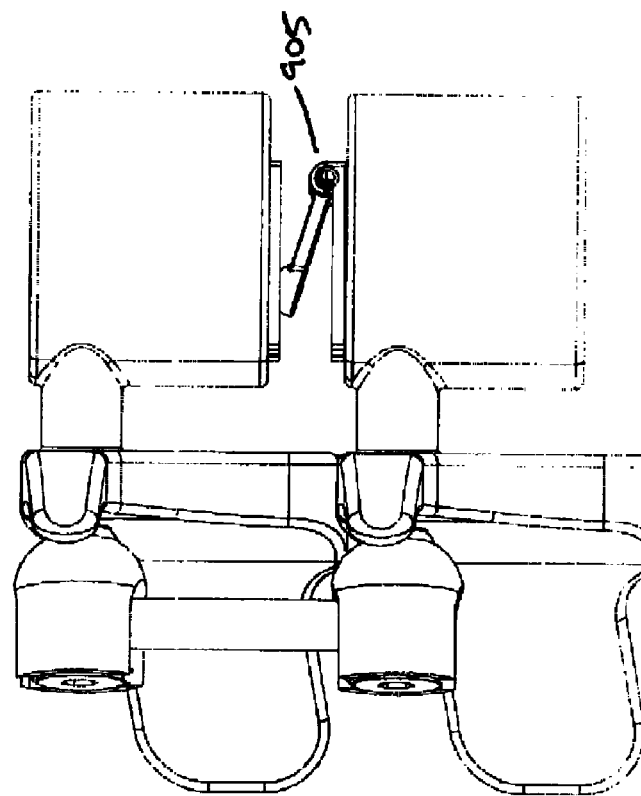
FIGS. 20B and 20C show an implant positioned in the disc space between the vertebral bodies V1 and v2 with supporting dynamic bone screws and rods.
Figure 20B:
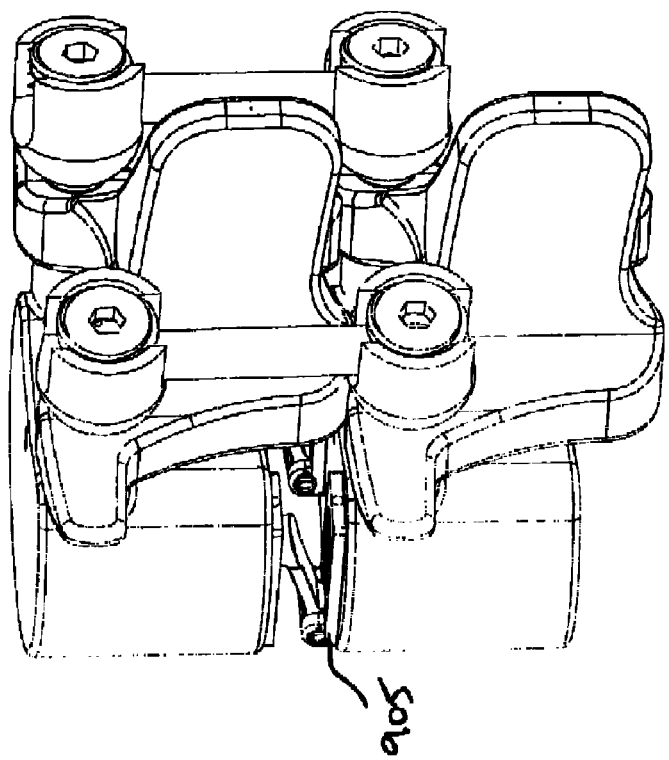
Figure 20D:
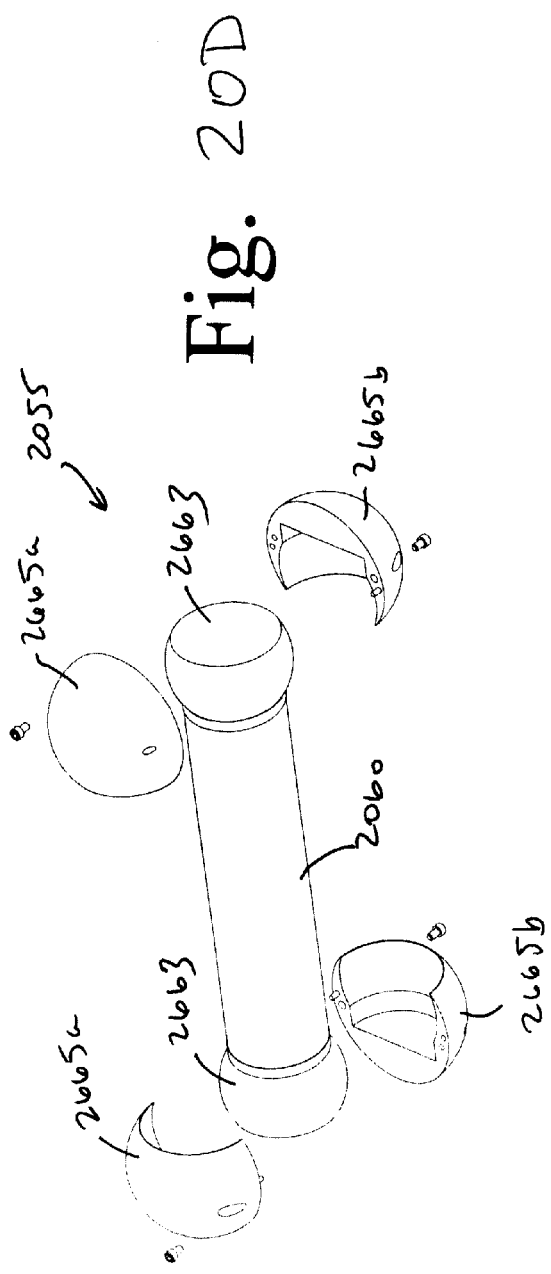
FIGS. 20D and 20E show embodiments of dynamic screws and rods.
Figure 20E:
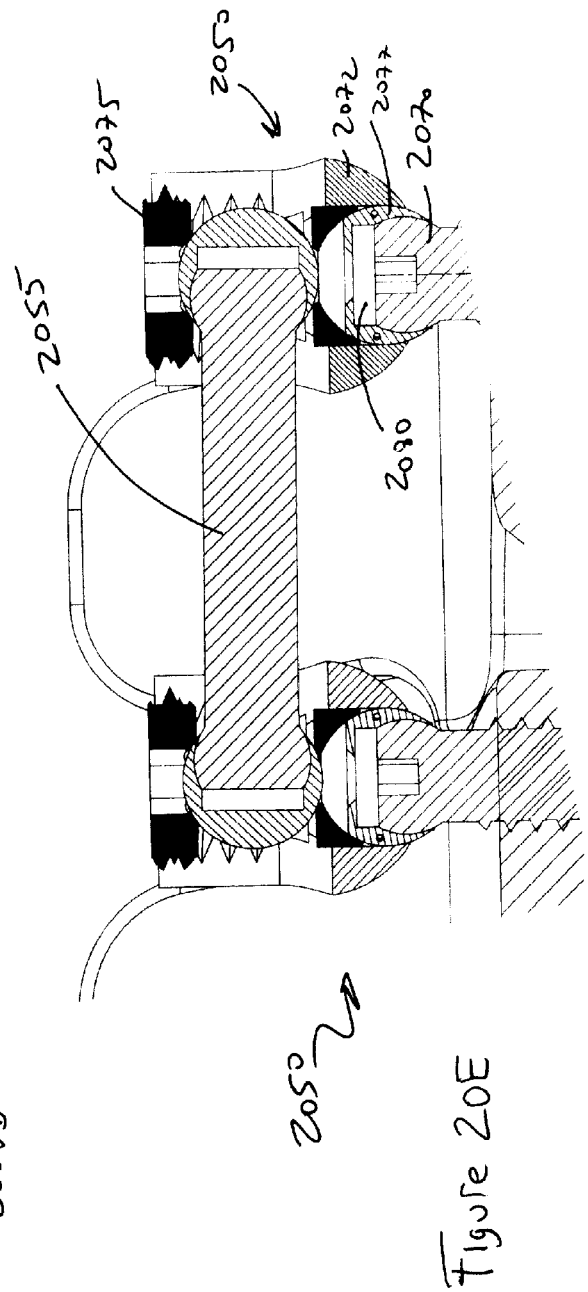

FIGS. 20B and 20C show the implant 905 positioned in the disc space between the vertebral bodies V1 and v2. The vertebral bodies are linked to one another via a pair of screw assembles 2050 and a rod 2055. The screw assemblies 2050 and rod assembly 2055 are dynamic in that they are adapted to permit at least some movement in response to loads. For example, FIG. 20D shows the dynamic rod assembly 2055, which includes dynamic terminii. The rod 2060 has a pair of heads 2663 that can each be positioned within housing members 2665*a* and 2665*b*. The members 2665*a* & *b* are joined to form the assembled inner housing member using threaded screws, but ratchets, clips, adhesives, or any other well-known technique for segment assembly may be alternatively used. The inner aspect of housing members 2665 contains a space that is positioned above the head 2663. The space within the housing members 2665 preferably contains a material or structure that resists movement of the head 2663 of the rod relative to the inner aspect of the inner housing members. With movement of head 2663 away from the predetermined neutral position within the inner housing members, the material/device in space applies a force to the head and resist any movement away from the neutral position.

With reference to FIG. 20D, the screw assemblies 2050 also have comparable dynamic arrangements. The bone screw assembly 2050 is dynamic in that it permits relative movement between the bone screw 2070 and the receiver 2072. When the assembly is locked by the advancement of locking nut 2075, an inner housing member 2077 is immobilized relative to the receiver 2072 and the contained rod 2055 while the bone screw is rigidly attached to the vertebral body. However, the head of the screw can move in a ball and socket manner within the inner housing member 2077 so as to permit continued movement between the bone screw and the interconnecting rod 2055.

When the screw head is moved out of a predetermined neutral position within the inner housing members, a material/device in space 2080 applies a force to the head of screw and resist any movement away from the neutral position. The assembly will return the screw and the attached bone to the neutral position once the deflecting force has dissipated.

Figure 20G:
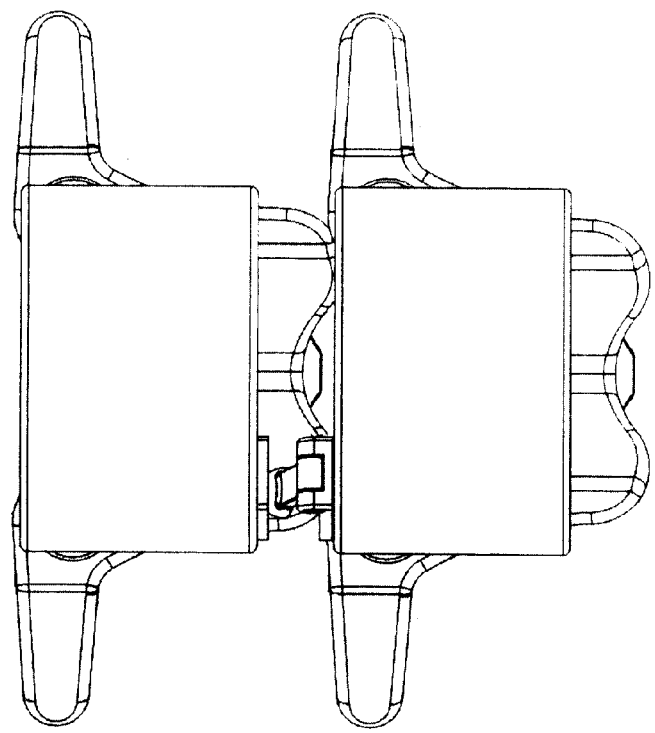
FIGS. 20F and 20G show alternative applications of the implant.
Figure 20F:
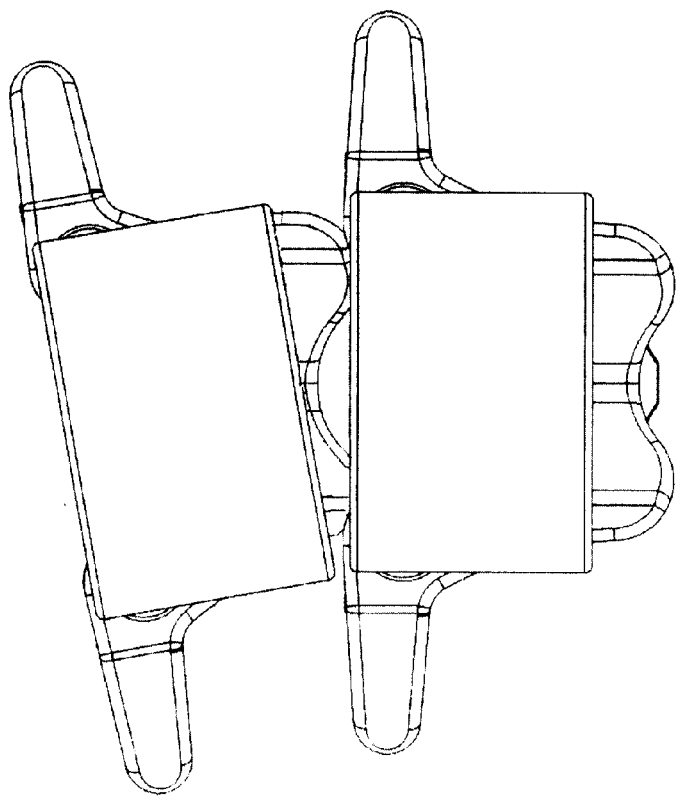

FIGS. 20F and 20G illustrate potential alternative applications of the device. FIG. 20F shows a deformity in the alignment of two vertebrae such that the vertebral bodies are misaligned in the coronal plane. The condition, termed scoliosis, can be corrected by placing a device into the disc space at the site of height loss—as shown in FIG. 20G.

FIG. 21 shows another embodiment of an implant 2105. The implant 2105 includes upper and lower components 2110 and 2115 and a middle component 2120. The middle component is similar to the middle component of the previous embodiment in that it permits controlled movement between the upper and lower components. However, the middle component 2120 of the implant 2105 includes a pair of lever members 2125 and 2130. Each of the lever members 2125 and 2130 is pivotably coupled to the lower component 2115 via a respective hinge member 2122. The hinge members 2120 are substantially identical to the hinge member shown in FIG. 13.

The lever member 2125 is substantially the same as the lever member of the previous embodiment although the lever member 2125 includes a seat 2135 that receives a bearing tip 2140 of the lever member 2130. The tip 2140 can slide within the confines of the seat 2135. Thus, the hinge members 2125 and 2130 collectively provide for relative movement between the upper and lower components of the implant 2105.

FIGS. 22 and 23 show another embodiment of an implant 2205. The implant 2205 includes upper and lower components 2210 and 2215 and a middle component 2220 that permits relative movement of the upper and lower components. The middle component comprises a pair of legs 2225 that are pivotably linked to a hinge member 2230. The legs 2225 include bearing ends that are slidably positioned within seats in the upper surface of the lower component 2215. The seats limit the amount of movement of the ends of the legs 2225. The arrangement of the legs 2225 and the hinge member 2230 impart a shock-absorbing quality to the device. Rotation may be prevented or preserved depending on the interaction of the ends of legs 2225 with the complimentary seats of the upper surface of the lower component 2215.

As shown in FIG. 23, the legs 2225 can move relative to the hinge member 2230 to permit controlled movement of the upper and lower components relative to one another. In addition, motion is further enhanced by the availability of a second bearing surface. Bearing surface 2239 is positioned atop hinge member 2230 and is affixed to the middle member of hinge 2230. Each leg member 2225 is affixed onto a side member of hinge 2230. The bearing surfaces 2239 may be of any known configuration such as, for example, the ball-and-socket arrangement of the prior embodiment (FIG. 10) or the bearing arrangement of the following embodiment (FIG. 24).

Figure 24:
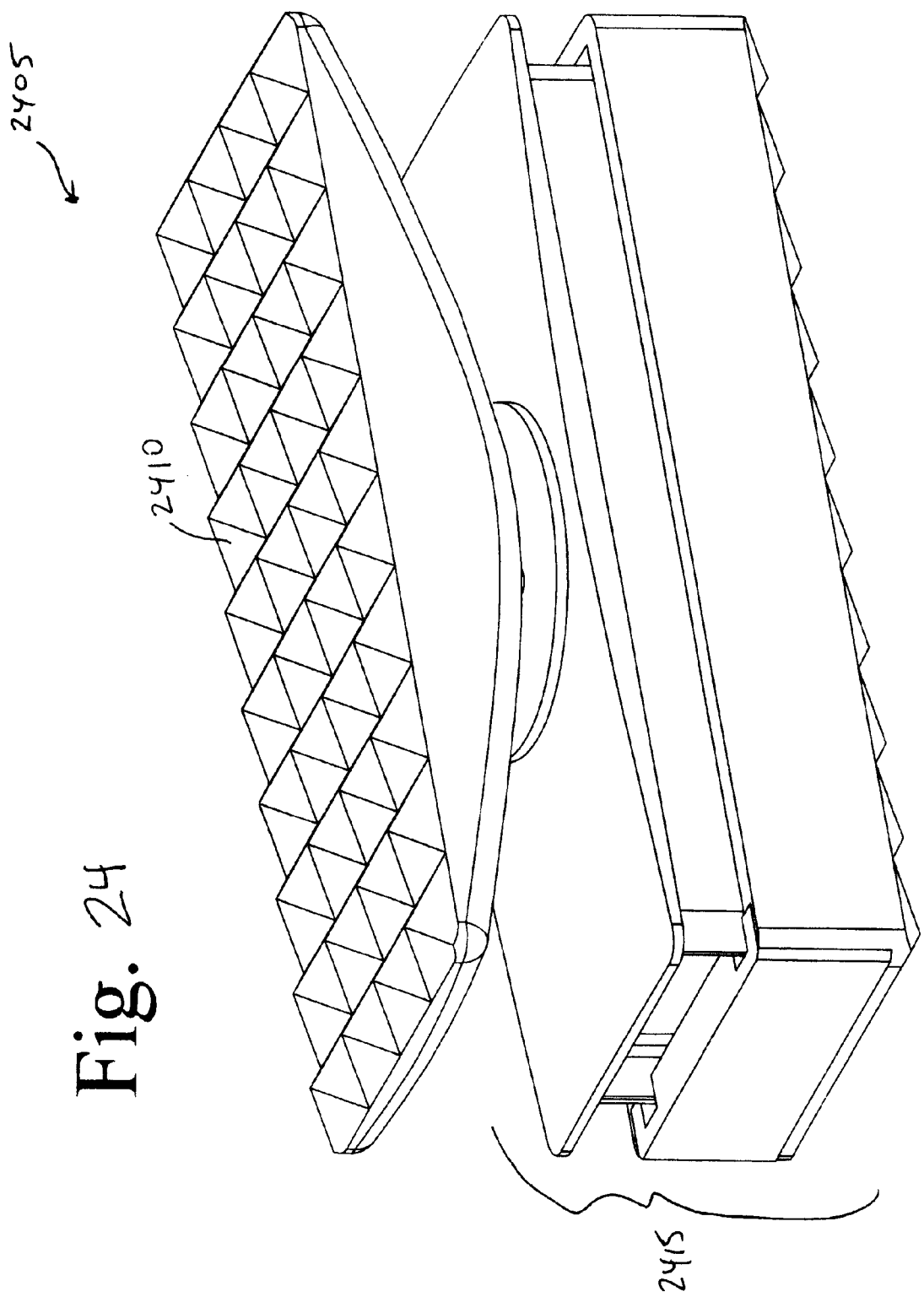
FIG. 24 shows another embodiment of an implant that is sized and shaped for implantation into the disc space.
Figure 25:
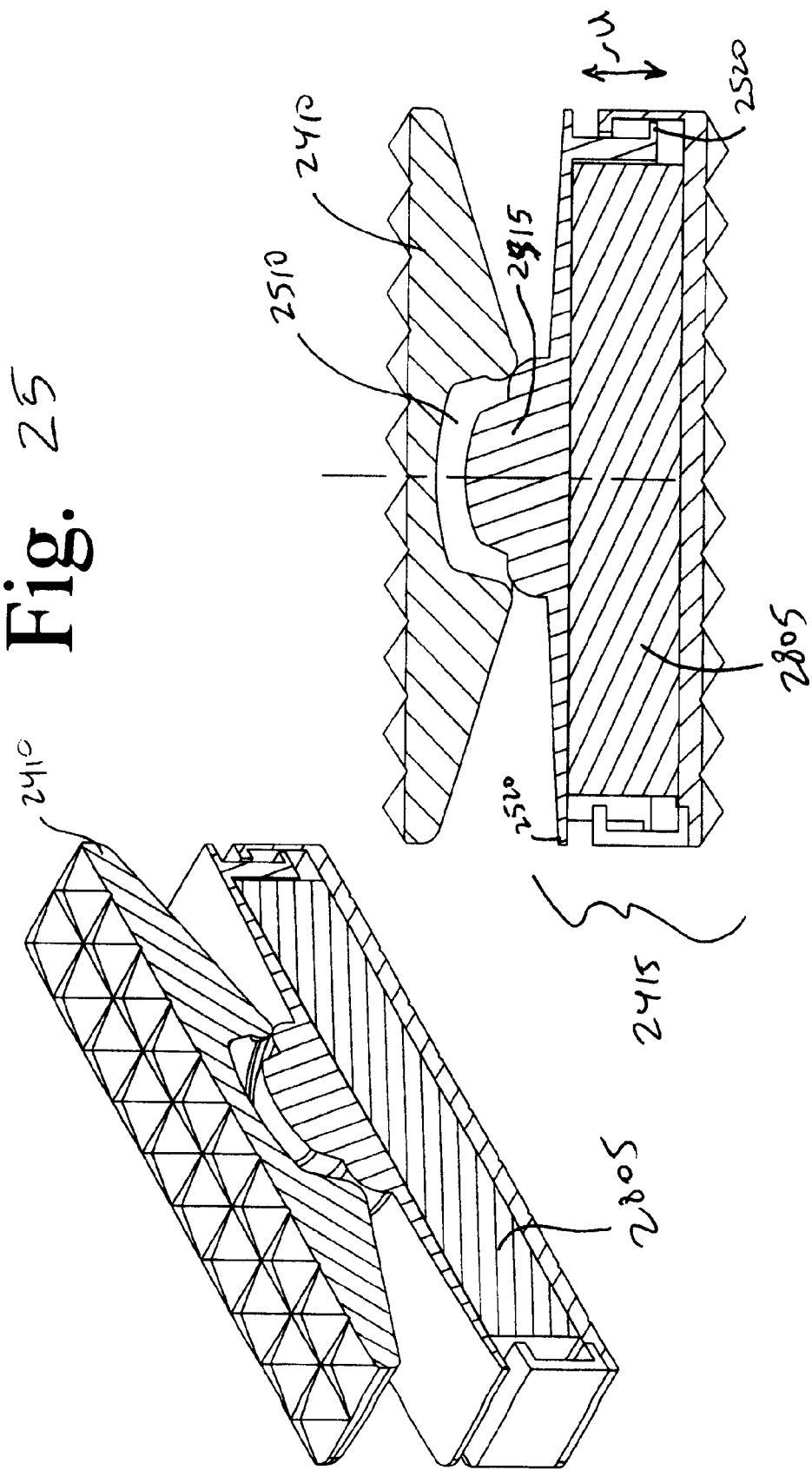
FIG. 25 shows perspective and cross-sectional views of the implant of FIG. 25.

FIG. 24 shows another embodiment of an implant 2405 that is sized and shaped for implantation into the disc space. FIG. 25 shows perspective and cross-sectional views of the implant 2405. The implant 2405 includes an upper component 2410 that is movably attached to a lower assembly 2415. The components of the lower assembly 2415 are described below. The upper component 2410 includes an abutment surface that is configured to abut against bone. The upper component includes an indentation or seat 2510 (FIG. 25) that movably mates with a protrusion 2515 on an upper portion of the lower assembly 2415. The seat 2510 and protrusion 2515 mate in such a way that the upper component 2410 can articulate relative to the lower assembly 2415 such as in response to loads.

The lower assembly 2415 is described in more detail with reference to FIGS. 26 and 27, which show partially exploded views of the implant 2405. The lower assembly 2415 includes an outer frame 2610 and an inner frame 2615 that removably attach to one another to define an internal cavity 2620. The outer frame and inner frame attach to one another in a manner that permits some movement therebetween such as along an upward and downward direction, as represented by the arrow U in FIGS. 25 and 27. In this regard, the inner and outer frames include shoulders 2520 (FIG. 25) that define the amount of relative movement. Thus, the upper component 2410 can articulate relative to the lower assembly while the lower assembly can itself change shape by virtue of the relative movement between the inner and outer frames.

FIG. 28 shows another exploded view of the implant 2405. The lower assembly 2415 can further include a malleable member 2805 that is sized and shaped to fit within the cavity 2620 defined by the inner and outer frames. The malleable member 2805 is made of a material that deforms in response to loads and returns to its original shape upon removal of the load. The malleable member 2805 is attached to a clip 2810 that can be attached to the inner and outer frames to secure the malleable member 2805 within the cavity 2620.

In use, the implant 2405 is initially implanted with the malleable member 2805 unattached to the lower assembly 2415. FIG. 29 shows the implant 2405 without the malleable member such that the inner frame 2615 is fully seated in the outer frame 2610. This permits the total implant height to be reduced. Once the implant 2405 is in a desired position in the disc space, the malleable member 2805 is placed within the cavity 2620 and locked into position. The presence of the malleable member raises the inner frame 2615 relative to the outer frame 2610 and increases the height of the implant. FIG. 30 shows the implant 2405 with the malleable member 2805 in the cavity 2620 and without any load on the implant. After a load is placed on the implant 31, the malleable member 2805 deforms in response to the load such that the height of the implant 2405 is reduced, as shown in FIG. 31.

Figure 32:
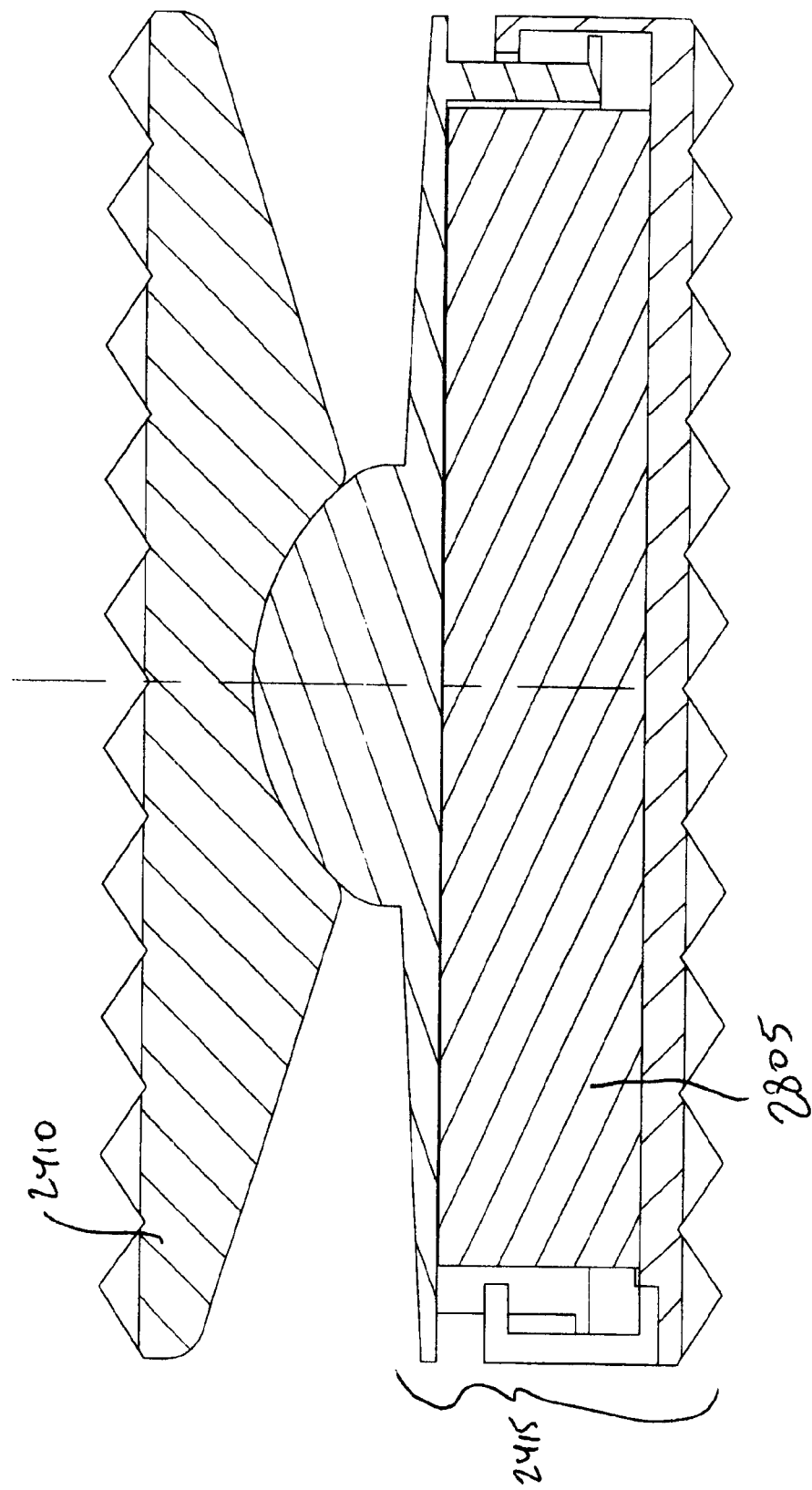
FIG. 32 shows another embodiment of an implant.
Figure 33:
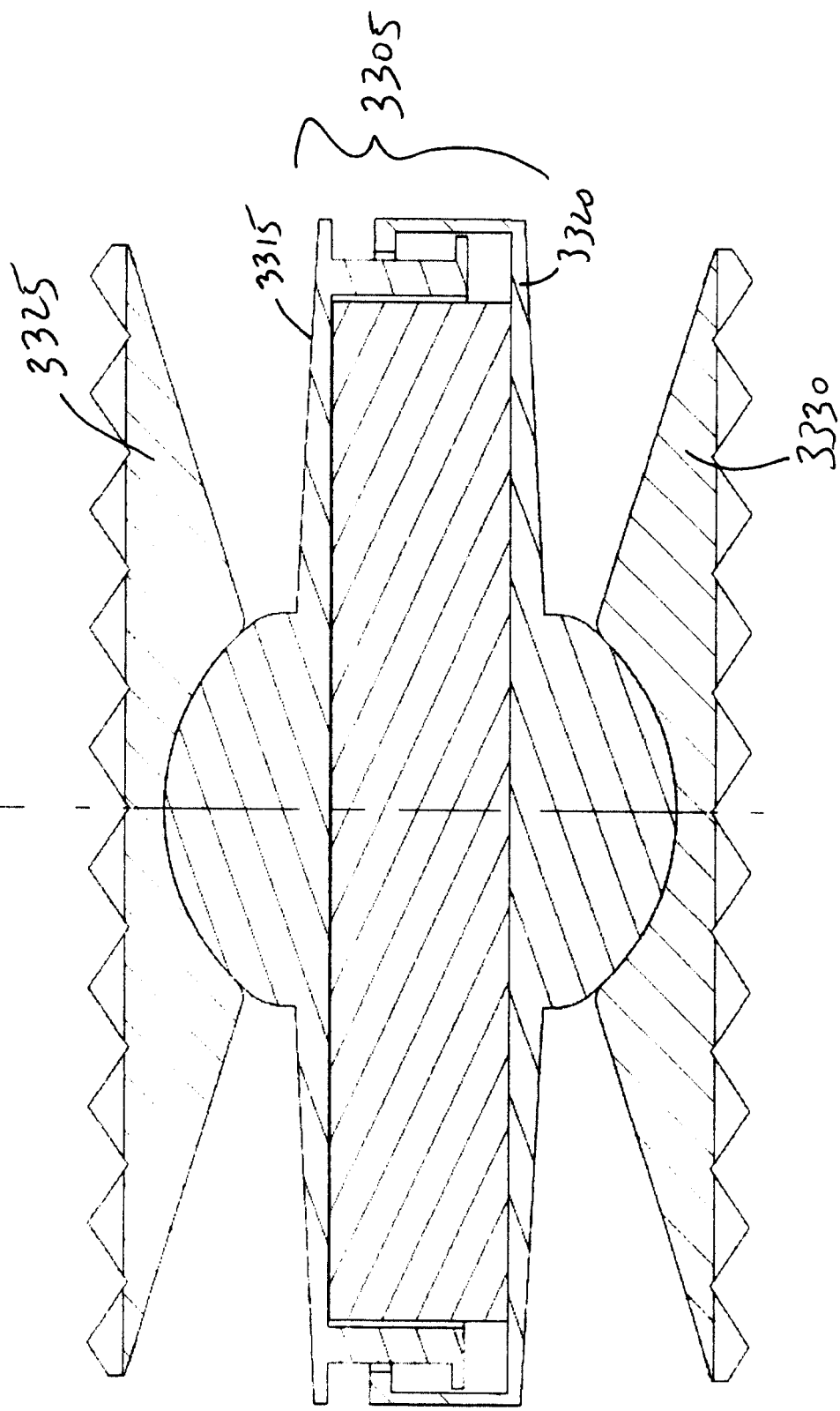
FIG. 33 shows another embodiment of an implant.

FIG. 32 shows another embodiment of an implant that is substantially similar to the implant shown in FIG. 24. In this embodiment, the lower assembly 2415 and upper component 2410 are movably coupled to one another in a ball-and-socket manner. The upper component 2410 has a socket that mates with a spherical protrusion on the lower assembly 2415. In yet another embodiment shown in FIG. 33, an implant includes a middle assembly that is similar to the lower assembly described above for the previous embodiment. The middle assembly includes inner and outer frames 3315 and 3320 that move relative to one another. A malleable member 2805 is positioned within the inner and outer frames. Upper and lower components 3325 and 3330 are movably attached to the middle assembly in a manner that permits articulation of the upper and lower components relative to the middle assembly.

FIG. 34 shows yet another embodiment of an implant 3405. The implant 3405 includes an upper component 3410 that movably mates with a lower component 3415. The lower component 3415 has a protrusion 3420 that movably sits within a seat 3425 on an interior surface of the upper component 3410. The seat 3425 includes three protrusions 3430. The protrusion has a toroid shape. The interaction of the toroid protrusion 3420 and the protrusions 3430 of the seat forms an articulation that has non-stationary center of rotation.

In the intact spine, the extent of rotation between adjacent vertebrae is limited and excessive rotation will significantly increase the stress forces applied to the facet joint. For this reason, it is desirable to limit the amount of rotation permitted by the disc prosthesis regardless of the specific design of the articulation surfaces. In the natural motion segment, the range of rotation varies with the amount of flexion between adjacent vertebrae. That is, the amount of rotation permitted by the motion segment is significantly greater in flexion than it is in extension. Recreation of this property within the disc prosthesis is desirable since a fixed range of rotation will likely produce an insufficient rotational range in flexion and an excessive range in extension.

Figure 35:
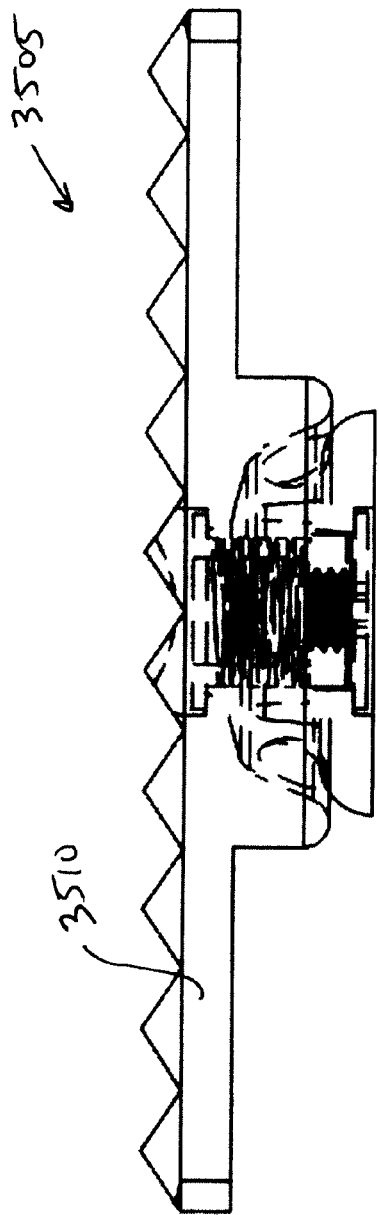
FIGS. 35 and 36 show cross-sectional views of another embodiment of an implant.
Figure 36:
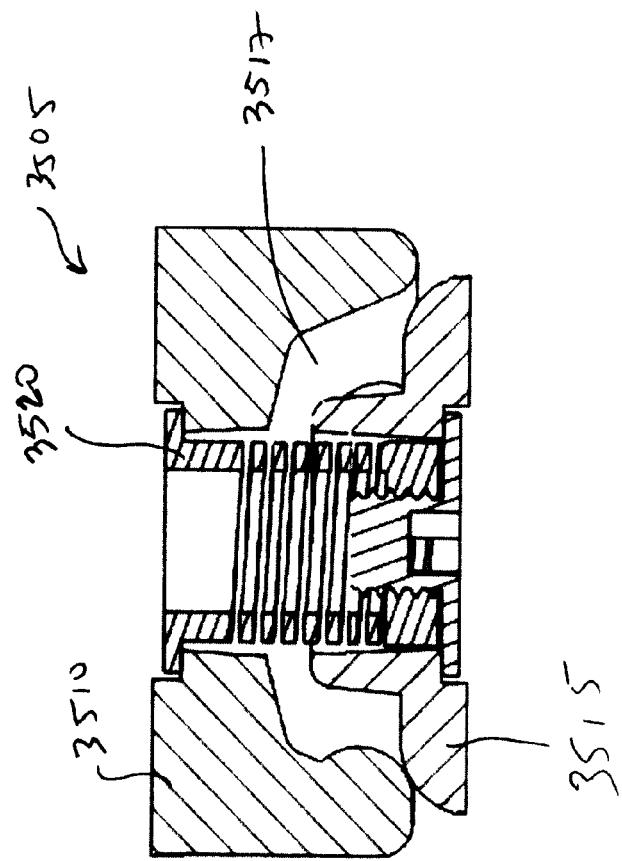

FIGS. 35 and 36 show cross-sectional views of another embodiment of an implant. The implant 3505 has an upper component 3510 and a lower component 3515 that are adapted to articulate relative to one another. Each of the upper and lower components has an abutment surface that abuts bone when the implant is positioned in a disc space. When the upper component and lower component are attached to one another, a space 3517 exists where the upper and lower components can move relative to one another. An articulating spring member 3520 is positioned within the space 3517. The spring member 3520 couples the upper and lower components together in a manner that permits relative movement but biases the upper and lower components toward default positions relative to one another.

Figure 38:
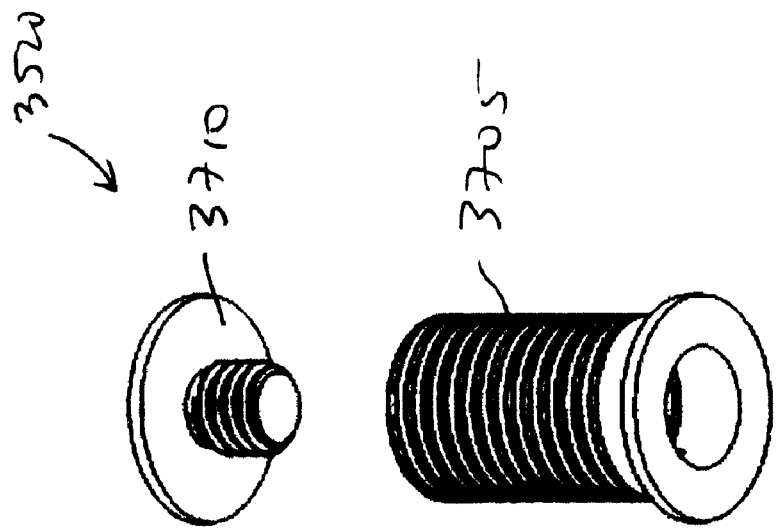
FIGS. 37 and 38 show a spring member of the implant of FIGS. 35 and 36.
Figure 37:
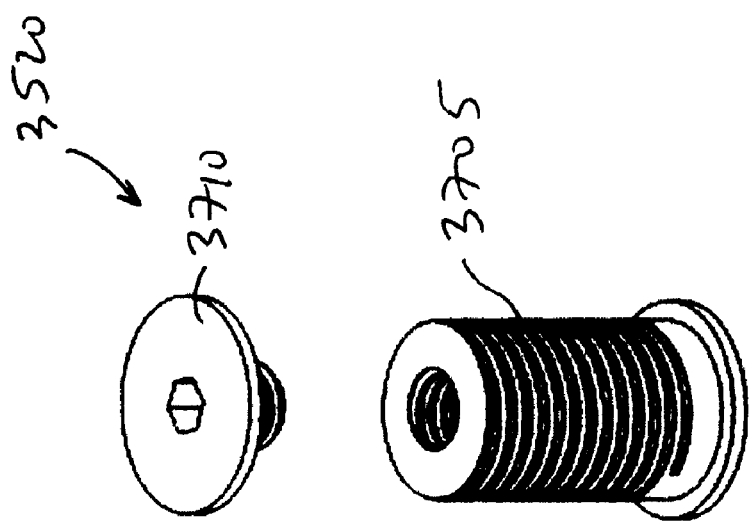

FIGS. 37 and 38 show the spring member of the implant 3505. The spring member 3520 includes a main body 3705 that removably attaches to a cap 3710. As shown in the cross-sectional views of FIGS. 35 and 36, the cap 3710 has a ledge that abuts the lower component 3515 and the main body 3705 has a shoulder that abuts the upper component 3510 to retain the spring member therein.

Figure 40A:
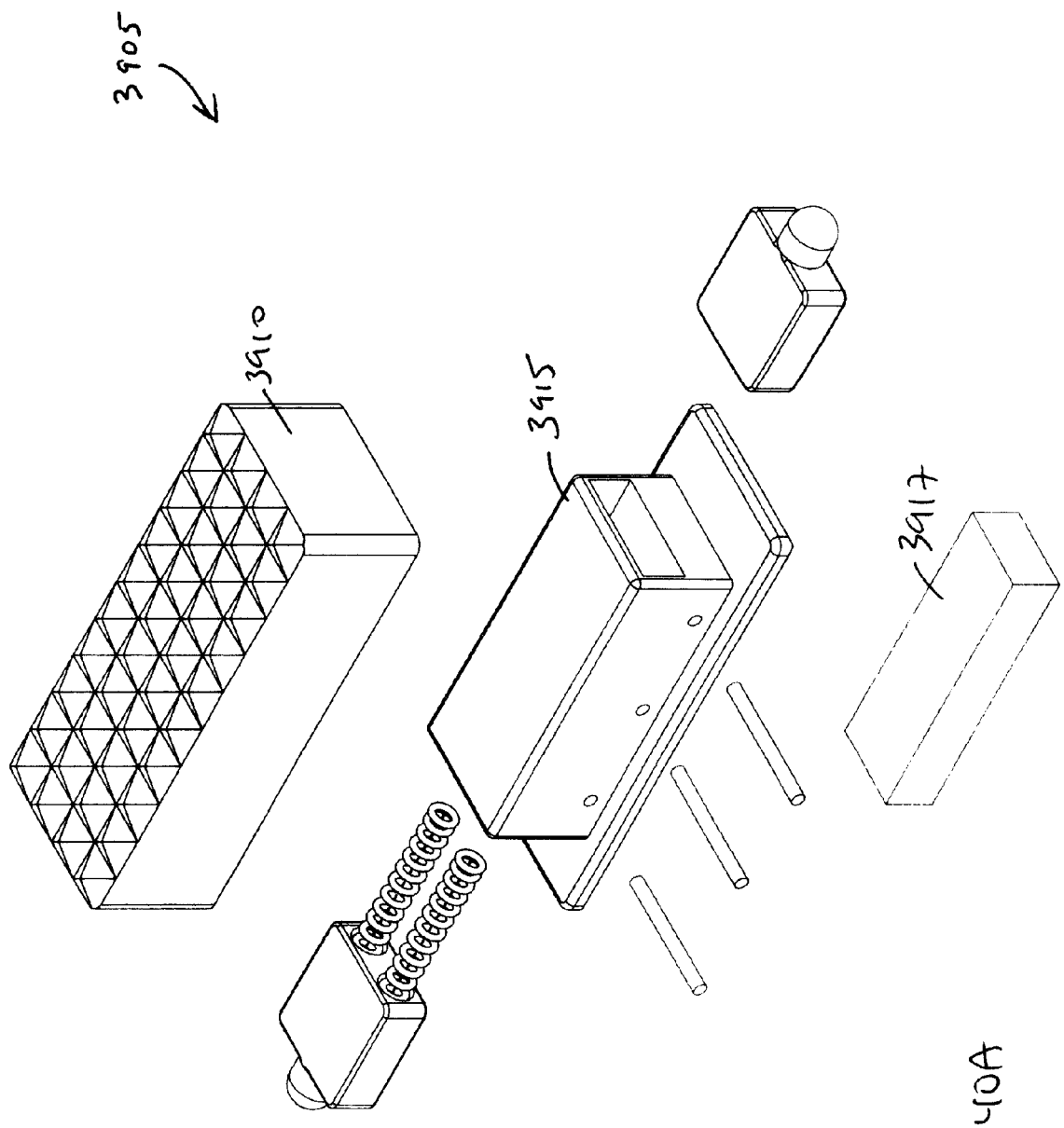
Figure 40B:
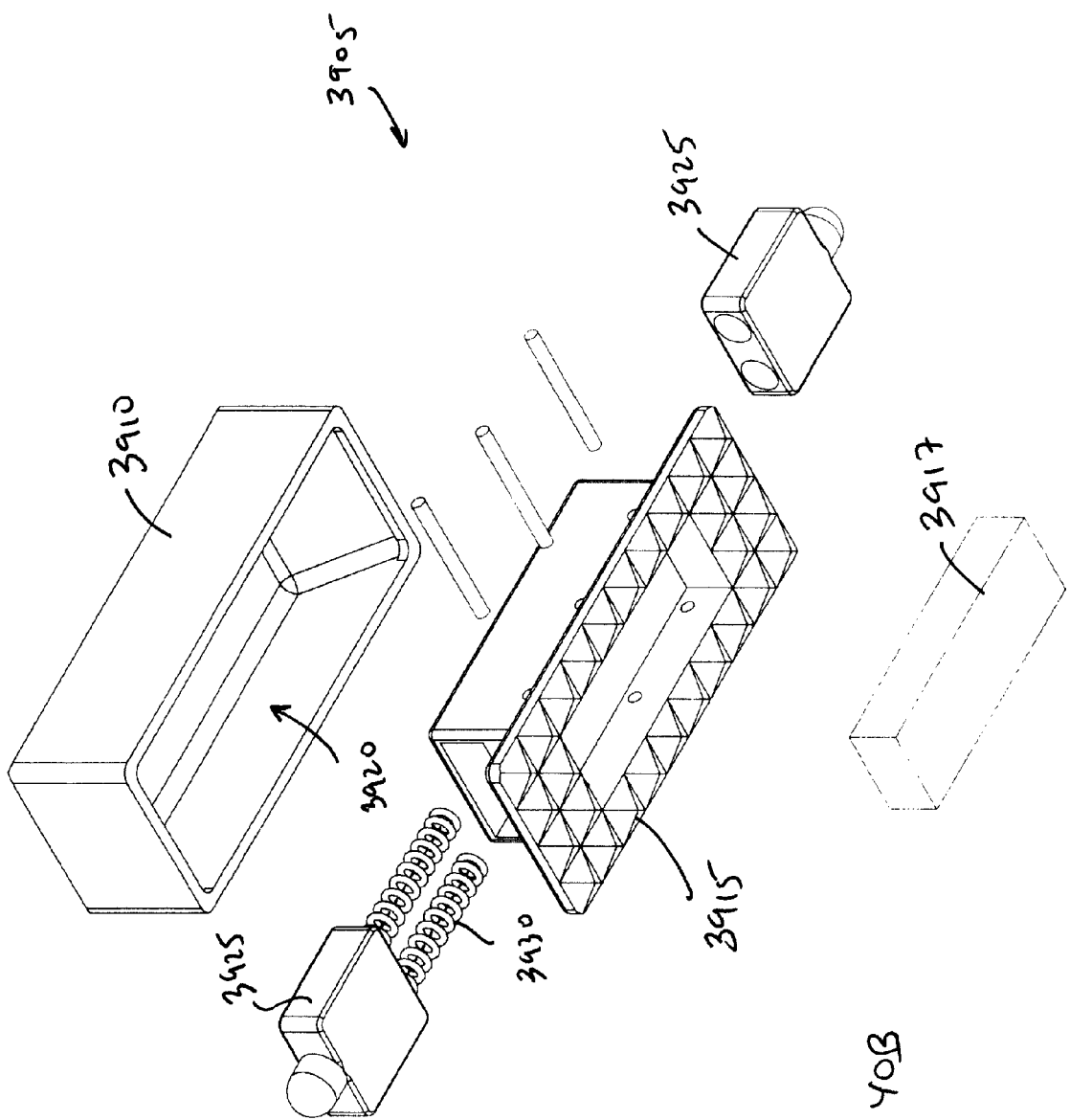

FIGS. 39 and 40A-40B show exploded views of another embodiment of an implant. The implant 3905 includes an upper component 3910 and a lower component 3915. Both the upper component and lower component have outer abutment surfaces for abutting against bone when in the disc space. A bone segment 3917 (preferably allograft), bone graft substitute, and/or a growth factor-soaked (such as BMP, etc.) material is positioned within a cavity in the lower component 3915 and, with implantation, will fuse with the adjacent vertebral surface so as to increase the device anchoring onto the vertebrae. While illustrated in the lower component 3915, this feature may be applied to either or both components.

Figure 42:
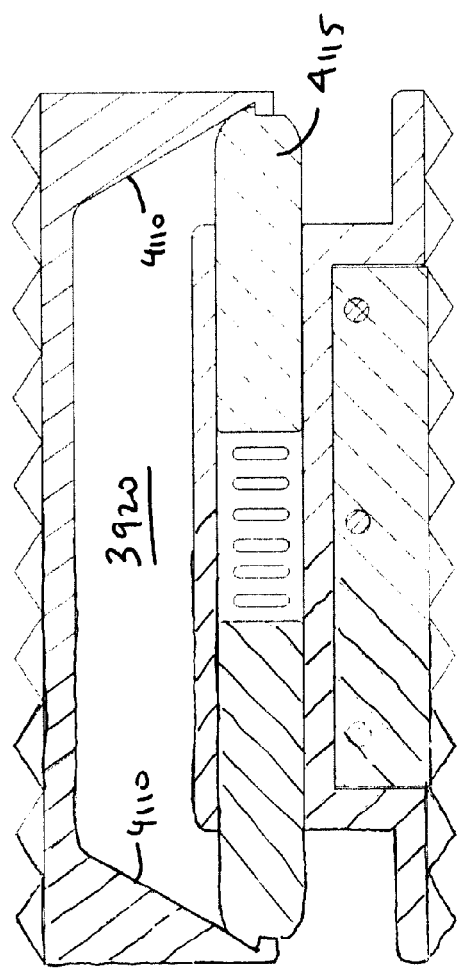
Figure 41:
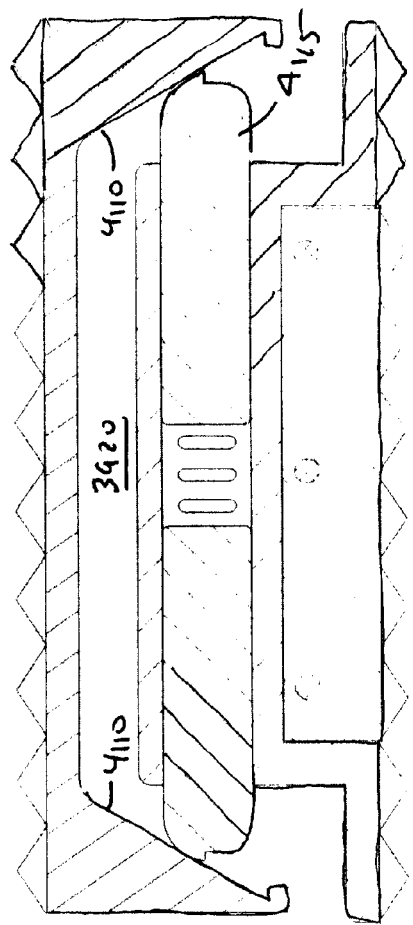

The upper component defines a cavity 3920 (FIG. 40B) in which the lower component is movably positioned. As shown in the cross-sectional views of FIGS. 41 and 42, the cavity 3920 has a pair of slopes walls 4110 that incline inwardly moving upward within the cavity. Member 4115 is formed of two blocks 3925 (FIG. 39) that are biased away from one another using at least one spring 3930. The interaction of the spherical tips of blocks 3925 and sloped walls 4110 will allow the upper component to rotate and translate relative to the lower component in various planes. In addition, vertical load applied to the implant will cause the upper component and lower components to move toward and away from one another. This load is opposed by the action of horizontally-placed springs 3930. Because of the action of the springs, member 4115 is biased outward and towards the sloped walls 4110. Member 4115 exerts a force against the sloped walls 4110 that forces the implant toward a default shape wherein the biasing member 4115 is positioned at the bottom portion of the cavity 3920, as shown in FIG. 42.

Figure 43:
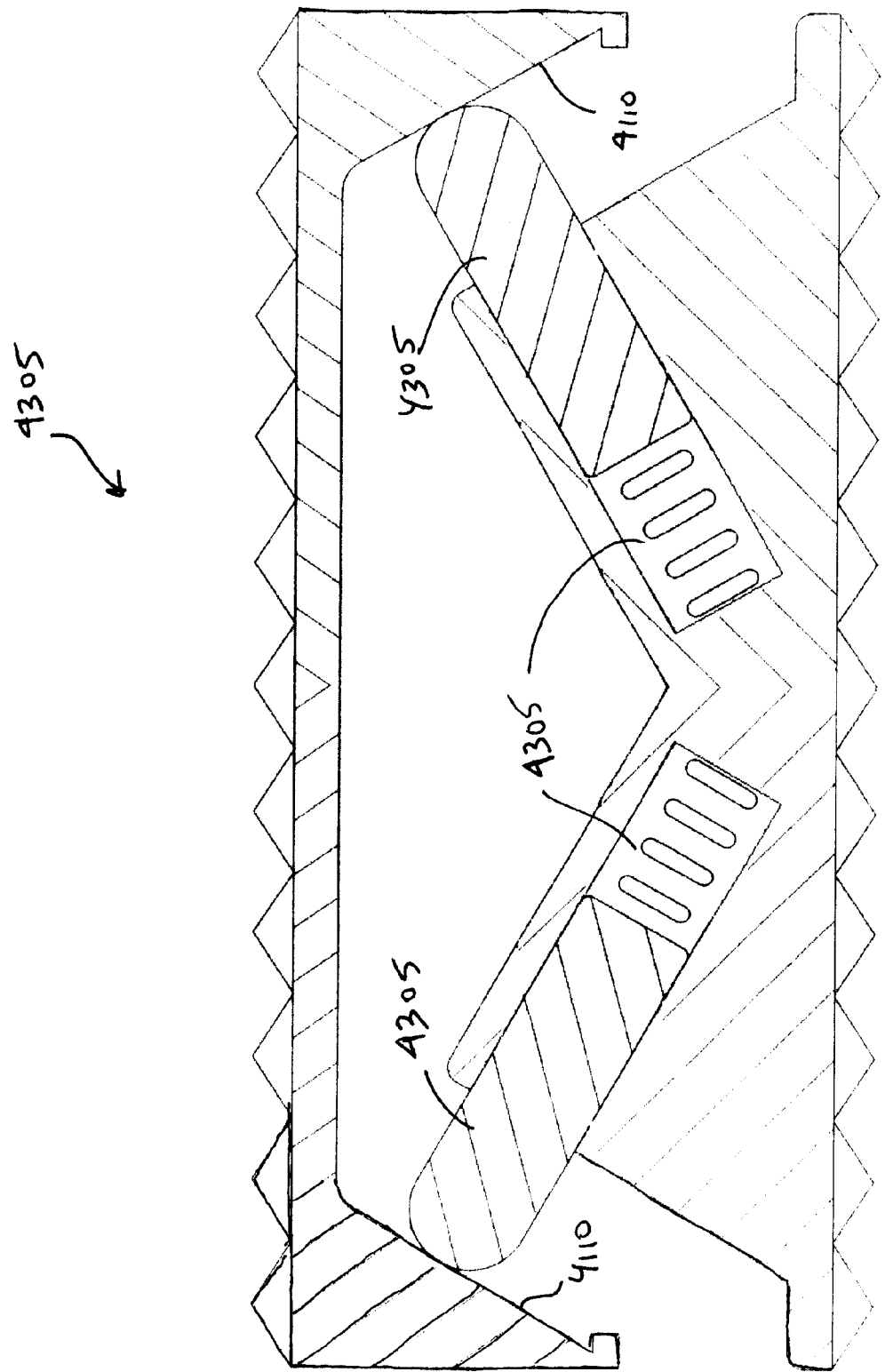
FIG. 43 shows another embodiment of an implant.

In another embodiment, shown in FIG. 43, an implant 4305 has a similar configuration as the implant 3905. However, the lower member includes a pair of biasing members 4305 that are biased outwardly toward the sloped walls 4110 via springs 4305.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed:

1. An orthopedic implant adapted to provide movement between two adjacent skeletal segments, comprising:

a first member that is adapted to be attached onto a first bone;

a second member that is adapted to be attached onto a second bone;

at least one flexible rotational articulation member that is contained within the implant and that provides at least partial movement between the first and second members about an axis of rotation that extends through the articulation member, wherein the articulation member is a flexure-based bearing, the articulation member having:

a plurality of sections that include at least one internal spring member capsuled within a cylindrical housing, wherein the cylindrical housing includes a first hollow cylindrical section and a second hollow cylindrical section, wherein each cylindrical section has an outer cylindrical surface and an internal cylindrical surface concentric with the internal cylindrical surface of the other cylindrical section, wherein the first and second cylindrical sections are coaxially aligned about the axis of rotation, and wherein the first and second cylindrical sections can rotate relative to one another and rotational movement is preserved after full implantation of the implant;

the first and second cylindrical sections being joined by the at least one spring member that extends from the internal cylindrical surface of the first cylindrical member to the internal cylindrical surface of the second cylindrical member; wherein the at least on internal spring member resists relative rotation of the first and second cylindrical sections along the axis of rotation away from a neutral rotation position in a rotational direction, wherein an extent of resistance to rotation increases with an extent of rotation of the first cylindrical section relative to the second cylindrical section in a rotational direction away from the neutral rotation position and wherein the at least one internal spring member returns the first and second cylindrical sections to the neutral rotation position after dissipation of a force producing the relative rotation of the cylindrical sections.

2. An orthopedic implant as in claim 1, wherein the at least one flexible rotational articulation member is a frictionless bearing.

3. An orthopedic implant as in claim 1, further comprising at least one coupler member movably positioned between the first and second members such that a first end of the at least one coupler member is rotatably attached to the at least one articulation member and a second end of the of the at least one coupler member interacts with at least one surface of the first member.

4. An orthopedic implant as in claim 3, wherein the at least one coupler member and the at least one surface of the first member comprises a ball and socket joint.

5. An orthopedic implant as in claim 4, wherein the second end of the at least one coupler member permits movement between the at least one coupler member and the second member about the axis of rotation of the at least one flexible rotational articulation member.

6. An orthopedic implant as in claim 1, wherein the implant is adapted to be placed into an inter-vertebral disc space between two vertebral bones and at least partially replace the function of a natural disc.

7. An orthopedic implant as in claim 1, wherein the implant is sized to be placed through a posterior surgical approach to the inter-vertebral disc space.

8. An orthopedic implant as in claim 7, wherein the implant is adapted to transition from a first state of a larger size to a second state of a smaller size.

9. An orthopedic implant as in claim 1, wherein the at least one internal spring member comprises at least two spring members that cross one another when viewed along the axis of rotation.

10. A surgical system comprised of:
an orthopedic implant as in claim 8; and
a vertebral distractor, wherein the distractor is adapted to engage at least one vertebral spinous process and apply a distractive force between adjacent vertebrae.

11. A surgical system comprised of:
an orthopedic implant as in claim 8; and
a vertebral distractor, wherein the distractor is adapted to engage at least one vertebral lamina and apply a distractive force between adjacent vertebrae.

* * * * *